United States Patent [19]

Akimoto et al.

[11] Patent Number: 5,459,129
[45] Date of Patent: * Oct. 17, 1995

[54] CONDENSED HETEROCYCLIC COMPOUNDS, THEIR PRODUCTION AND USE

[75] Inventors: Hiroshi Akimoto, Kobe; Kazuyoshi Aso; Koichiro Ootsu, both of Osaka, all of Japan

[73] Assignee: Takeda Chemical Industries, Ltd., Osaka, Japan

[*] Notice: The portion of the term of this patent subsequent to Dec. 7, 2010 has been disclaimed.

[21] Appl. No.: 112,795

[22] Filed: Aug. 27, 1993

Related U.S. Application Data

[62] Division of Ser. No. 806,893, Dec. 16, 1991, Pat. No. 5,268,362.

[30] Foreign Application Priority Data

Dec. 14, 1990 [JP] Japan .................. 2-402433

[51] Int. Cl.$^6$ .................. A61K 38/05; A61K 38/06; A61K 38/07; A61K 38/08
[52] U.S. Cl. .................. 514/17; 514/18; 514/19; 514/253; 514/254; 514/255; 514/256; 514/299; 514/300; 514/301; 514/302; 514/303; 530/329; 530/330; 530/331; 544/278; 544/280; 546/114; 546/115; 546/116; 546/117; 546/118; 546/119; 546/120
[58] Field of Search .................. 544/278, 280; 546/114, 115, 116, 117, 118, 119, 120; 514/253, 254, 255, 256, 299, 300, 301, 302, 303, 17, 18, 19; 530/329, 330, 331

[56] References Cited

U.S. PATENT DOCUMENTS

| | | | |
|---|---|---|---|
| 4,996,206 | 2/1991 | Taylor et al. | 514/258 |
| 4,997,838 | 3/1991 | Akimoto et al. | 514/258 |
| 5,028,608 | 7/1991 | Taylor et al. | 514/258 |

FOREIGN PATENT DOCUMENTS

| | | |
|---|---|---|
| 268377 | 5/1988 | European Pat. Off. . |
| 402903 | 12/1990 | European Pat. Off. . |
| 418924 | 3/1991 | European Pat. Off. . |
| 434426 | 6/1991 | European Pat. Off. . |
| 431953 | 6/1991 | European Pat. Off. . |
| 438261 | 7/1991 | European Pat. Off. . |

OTHER PUBLICATIONS

Catalog Handbook of Fine Chemicals by Aldrich, pp. 297–298 & 738–739.

*Primary Examiner*—Mukund J. Shah
*Assistant Examiner*—Matthew V. Grumbling
*Attorney, Agent, or Firm*—Foley & Lardner

[57] ABSTRACT

A novel compound of the formula:

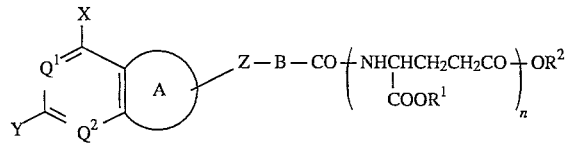

wherein a ring A stands for an optionally substituted 5-membered ring; B stands for an optionally substituted divalent cyclic or chain group; either one of $Q^1$ and $Q^2$ stands for N and the other stands for N or CH; X stands for an amino group, hydroxyl group or mercapto group; Y stands for H, halogen atom or a group bonded through C, N, O or S; Z stands for a straight-chain divalent group having 2 to 5 atoms constituted of optionally substituted carbon atoms or constituted of optionally substituted carbon atoms and one optionally substituted hetero-atom; $COOR^1$ and $COOR^2$ independently stand for an optionally esterified carboxyl group; n denotes an integer of 2 to 6; and $R^1$ may be different in each of n repeating units, or their salts and it is useful as a therapeutic drug for tumor in mammals.

13 Claims, No Drawings

CONDENSED HETEROCYCLIC COMPOUNDS, THEIR PRODUCTION AND USE

This application is a divisional of Ser. No. 07/806,893, filed Dec. 16, 1991, now U.S. Pat. No. 5,268,362.

FIELD OF THE INVENTION

This invention relates to a novel condensed heterocyclic oligoglutamate useful as an anti-tumor agent, its production and use.

BACKGROUND OF THE INVENTION

Folic acid and its related compounds are carriers of one-carbon (C1) units in a living body derived from formic acid or formaldehyde, acting as a coenzyme in various enzymatic reactions such as those in biosynthesis of nucleic acid, in metabolism of amino acids and peptides and in generation of methane. Particularly for metabolism or transfer reaction of C1 units in biosynthesis of nucleic acid, i.e. the purine synthetic pathway and the thymidine synthetic pathway, folic acid and its related compounds are essential. Usually, folic acid is efficiently stored intracellularly as oligoglutamates by glutamylation with folylpolyglutamyl synthase after being transformed into tetrahydrofolic acid being an activated coenzyme by reduction in two steps. This tetrahydrofolic acid and its oligoglutamates display biological activity as coenzyme in various enzymatic reactions in the state of combination with C1 units.

On the other hand, Amethopterin (methotrexate:MTX) and its related compounds are known as drugs to inhibit the reduction from dihydrofolic acid into tetrahydrofolic acid by coupling strongly with the dominant enzyme (dihydrofolate reductase) in this reduction. These drugs have been developed as antitumor drugs because they may disturb the DNA synthesis and consequently cause cell death, and are used clinically. Further, antifolates, having an action mechanism different from inhibition of dihydrofolate reductase, i.e. a tetrahydroaminopterin antitumor agent (5,10-dideaza-5,6,7,8-tetrahydroaminopterin: DDATHF), whose main action mechanism consists in inhibition of glycinamide ribonucleotide transformylase concerned in the initial stage of purine biosynthesis [Journal of Medicinal Chemistry, 28, 194 (1985)], and a quinazoline antitumor agent (2-desamino-2-methyl-10-propargyl-5,8-dideazafolate: DMPDDF), whose main action mechanism consists in inhibition of thymidylate synthase concerned in transformation of deoxyuridin monophosphate to deoxythimidine monophosphate [British Journal of Cancer 58, 241 (1988)], and their oligoglutamates [Journal of Medicinal Chemistry, 29, 1754 (1986) and 31, 181 (1988)] have been reported. However, their oligoglutamates have as a condensed heterocyclic moiety a condensed ring formed with two 6-membered rings but do not have a condensed ring formed with a 5-membered ring and 6-membered ring.

And, recently, it has been reported that, besides these antifolates and oligoglutamates having a condensed ring formed with a 6-membered ring and a 6-membered ring, compounds having a condensed ring formed with a 6-membered ring and a 5-membered ring, i.e. a pyrrolo[2,3-d] pyrimidine skeleton, have also excellent anti-tumor activity. For example, EP-A-334636 describes a compound of the formula:

(A)

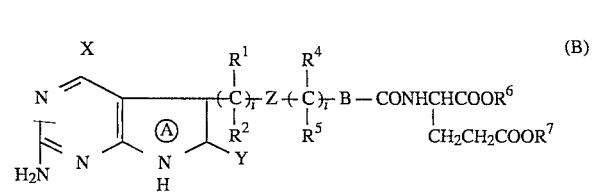

wherein a ring Ⓐ is a pyrrole or pyrroline ring, X is an amino group or a hydroxyl group, Y is a hydrogen atom, an amino group or a hydroxyl group, R is a hydrogen atom, a fluorine atom, an alkyl group, an alkenyl group or an alkynyl groups, —COOR$^1$ and —COOR$^2$ are independently carboxyl group which may be esterified and n is an integer of 2 to 4, and R may be different in each of the n repeating units, and salts thereof have excellent antitumor effects, and can be used as antitumor agents in mammals, EP-A-400562 describes a compound of the formula:

(B)

wherein a ring Ⓐ is a pyrrole ring which may be hydrogenated, X is an amino, hydroxyl or mercapto group, Y is a hydrogen atom or a hydroxyl group, $R^1$, $R^2$, $R^4$ and $R^5$ may be the same or different and are each a hydrogen atom, a lower hydrocarbon radical or a chemical bond, Z is —O—, a group of the formula —S—(O)n- in which n is an integer of 0 to 2 or a group of the formula $$-\underset{|}{\overset{R^3}{N}}-$$

in which $R^3$ is a hydrogen atom, a lower hydrocarbon radical optionally having substituent (s), a group attached through —CO— or —S(O)m (m is 1 or 2) or a chemical bond, —Ⓑ— is a divalent cyclic group optionally having substituent(s) of a lower alkylene group optionally having substituent (s), —COOR$^6$ and —COOR$^7$ may be the same or different and are each a carboxyl group which may be esterified, and i and j are an integer of 0 to 3 provided that i+j=1 to 3, or its salt thereof, which is useful an antitumor agent, U.S. Pat. No. 4,996,206 describes a compound of the formula:

(C)

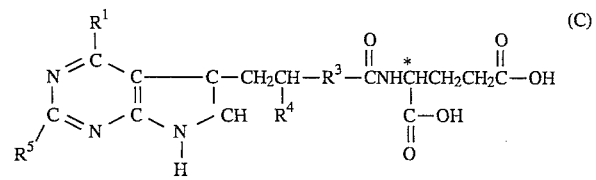

in which $R^1$ is —OH or —NH$^2$;

$R^3$ is 1,4-phenylene or 1,3-phenylene unsubstituted or substituted with chloro, fluoro, methyl, methoxy, or trifluoromethyl: thienediyl or furanediyl each unsubstituted or substituted with chloro, fluoro, methyl, methoxy, or trifluoromethyl: cyclohexanediyl: or alkanediyl:

$R^4$ is hydrogen, methyl, or hydroxymethyl:

$R^5$ is hydrogen or alkyl of 1 to 6 carbon atoms:

the configuration about the carbon atom designated * is S: and the pharmaceutically acceptable salts thereof, which is used as antineoplasmic agents, and U.S. Pat. No. 5,028,608 describes a compound of the formula:

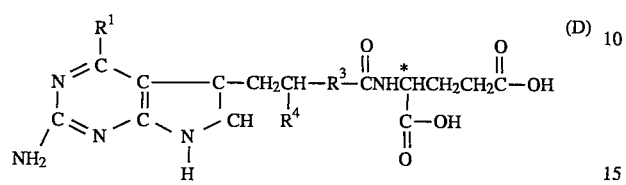

in which $R^1$ is —OH or —$NH_2$:

$R^3$ is thienediyl or furanediyl each unsubstituted or substituted with chloro, fluoro, methyl, methoxy, or trifluoromethyl; cyclohexanediyl; or alkanediyl;

$R^4$ is hydrogen, methyl, or hydroxymethyl; the configuration about the carbon atom designated * is S: and the pharmaceutically acceptable salts thereof, which is used as antineoplasmic agents.

However, their compounds (A), (B), (C) and (D) having a pyrrolo[2,3-d] pyrimidine skeleton are not in the form of oligoglutamates at their side chain.

What is now specifically desired in the field of cancer therapy is the creation of drugs which have toxicities highly specific to cancer cells based on the action mechanism having excellent therapeutic effects. The MTX whose principal action mechanism consists in inhibition of dihydrofolate reductase is clinically used widely, though the therapeutic effect is still unsatisfactory because is has relatively strong toxicity with little effect on solid cancer.

SUMMARY OF THE INVENTION

As the result of the inventors' diligent research under the circumstances described above, they have found that novel oligoglutamates having a ring condensed heterocyclic formed with certain 6-membered ring and 5-membered ring are stored in cells efficiently, and perform excellent anti-tumor action while showing highly specific toxicities to various cells, especially to solid tumors, by inhibiting one or more pathways of biosynthesis of nucleic acid, with which folic acid and its related compounds are concerned and have an excellent solubility to water.

DETAILED DESCRIPTION OF THE INVENTION

Namely, this invention provides (1) compounds of the formula (I):

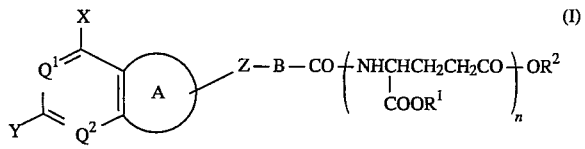

wherein a ring A stands for an optionally substituted 5-membered ring; B stands for an optionally substituted divalent cyclic or chain group; either one of $Q^1$ and $Q^2$ stands for N and the other stands for N or CH; X stands for an amino group, hydroxyl group or mercapto group; Y stands for hydrogen atom, a halogen atom or a group bonded through carbon, nitrogen, oxygen or sulfur atom; Z stands for a straight-chain divalent group having 2 to 5 atoms constituted of optionally substituted carbon atoms or constituted of optionally substituted carbon atoms and one optionally substituted hetero atom; $COOR^1$ and $COOR^2$ independently stand for an optionally esterified carboxyl group; n denotes an integer of 2 to 6; and R may be different in each of n repeating units, or their salts, (2) a method of producing a compound of the formula (I) or a salt thereof, which is characterized by allowing a compound of the formula (II):

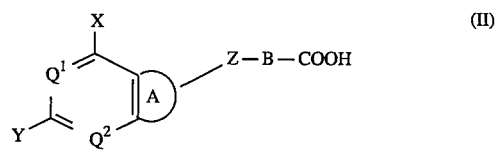

wherein the symbols are of the same meaning as defined in the formula (I), or a reactive derivative thereof at the carboxyl group to react with a compound of the formula (III):

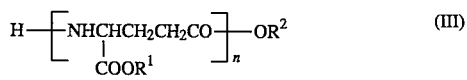

wherein the symbols are of the same meaning as defined in the formula (I), and (3) an anti-tumor composition comprising a compound of the formula (I) or a salt thereof.

Among the compounds of the formula (I), especially preferable ones are those represented by the formula (IV):

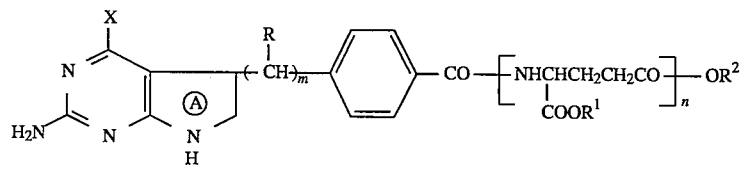

wherein a ring Ⓐ stands for an optionally hydrogenated pyrrole ring, R stands for hydrogen or a lower alkyl group, m denotes an integer of 2 to 4, R may be different in each of m repeating units, and the other symbols are of the same meaning as defined in the formula (I).

When X in the formulae described above is a hydroxyl group or mercapto group, each of the compounds (I), (II) and (IV) may exist as an equilibrium mixture of the respective tautomers. The following partial structural formulae show the sites of the structure which are subject to tautomerism, with the equilibrium relationship between the tautomers.

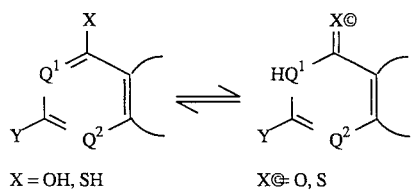

X = OH, SH    X⊖= O, S

For the convenience of description, hydroxyl forms or mercapto forms and the corresponding names are described throughout this specification, but the corresponding oxo forms or thio forms are included as well.

There may be two or more asymmetric centers in the compounds (I) or salts thereof of this invention, and the absolute configuration of the asymmetric centers may be S, R or RS mixed form, except that the absolute configuration at the asymmetric carbon atom in the side chain derived from glutamic acid is always S(L).

Therefore, the compounds (I) or salts thereof may have two or more diastereomers which, when necessary, can easily be separated by a conventional method for separation and purification. All of the diastereomers which can be separated thus are included in this invention.

Examples of the 5-membered cyclic groups shown by the ring A in the formula (I) described above include cyclic groups composed of carbon atoms, or carbon atoms and one hetero atom (nitrogen atom, oxygen atom or sulfur atom), and these cyclic groups may be substituted.

Examples of the ring of these cyclic groups include cyclopentadiene, cyclopentene, furan, dihydrofuran, thiophene, dihydrothiophene, thiophen-1-oxide, dihydrothiophen-1-oxide, thiophen-1,1-dioxide, dihydrothiophen-1,1-dioxide, pyrrole, pyrroline, N-substituted pyrrole and N-substituted pyrroline.

These cyclic groups may have 1 or 2 substituents at any possible position, and examples of said substituents include a $C_{1-3}$ alkyl group (e.g. methyl, ethyl, propyl, iso-propyl group), $C_{2-3}$ alkenyl group (e.g. vinyl, 1-methylvinyl, 1-propenyl, allyl, allenyl group), $C_{2-3}$ alkynyl group (e.g. ethynyl, 1-propynyl, propargyl group), $C_{3-6}$ cycloalkyl group (e.g. cyclopropyl group), halogen atom, (e.g. fluorine, chlorine, bromine, iodine), $C_{1-4}$ alkanoyl group (e.g. formyl, acetyl, propionyl, butyryl, isobutyryl group), benzoyl group, substituted benzoyl group, preferably a benzoyl group substituted with 1 to 3 substituents selected from a halogen atom and a $C_{1-4}$ alkoxy group (e.g. p-chlorobenzoyl, p-methoxybenzoyl, 3,4,5-trimethoxybenzoyl group), cyano group, carboxyl group, carbamoyl group, nitro group, hydroxyl group, hydroxy-$C_{1-3}$ alkyl group (e.g. hydroxymethyl group, hydroxyethyl group), $C_{1-3}$ alkoxy-$C_{1-3}$ alkyl group (e.g.methoxymethyl group, methoxyethyl group, ethoxyethyl group), $C_{1-3}$ alkoxy group (e.g. methoxy, ethoxy, propoxy group), mercapto group, $C_{1-3}$ alkylthio group (e.g. methylthio, ethylthio, propylthio group), amino group, $C_{1-4}$ substituted amino group, preferably an amino group substituted with one or two $C_{1-4}$ alkyl groups (e.g. methylamino, ethylamino, dimethylamino, diethylamino group), and $C_{1-2}$ alkanoylamino group (e.g. formamido, acetamido group).

Examples of the N-substituents at the N-substituted pyrrole and N-substituted pyrroline rings include, the above-mentioned $C_{1-3}$ alkyl group, $C_{2-3}$ alkenyl group, $C_{3-6}$ cycloalkyl group (e.g. cyclopropyl group), $C_{1-4}$ alkanoyl group, benzoyl group, substituted benzoyl group, hydroxyethyl group, methoxyethyl group and ethoxyethyl group, and besides a phenyl group, a substituted phenyl group, preferably a phenyl group substituted with 1 to 3 substituents selected from a halogen atom and a $C_{1-4}$ alkoxy group (e.g. p-chlorophenyl, p-methoxyphenyl, 3,4,5-trimethoxyphenyl group), a benzyl group or substituted benzyl group, preferably a benzyl group substituted with 1 to 3 substituents selected from a halogen atom, a $C_{1-4}$ alkoxy group and phenyl (e.g. p-chlorobenzyl, p-methoxybenzyl, diphenylmethyl group). The ring A can be bonded to Z at any possible position, and, in the case of the ring A being a N-substituted pyrrole or N-substituted pyrroline ring, the bondage may occur at the N-substituted portion.

Preferable cyclic groups in an optionally substituted divalent cyclic group shown by B include a 5- or 6-membered divalent cyclic group optionally containing a hetero atom (e.g. N, O, S), having bonding hands at positions which are not adjacent to each other in the ring. Examples of the 5-membered divalent cyclic group shown by B include 1,3- or 3,5-cyclopentadien-1,3-ylene, cyclopenten-(1,3-, 1,4- or 3,5-)ylene, cyclopentan-1,3-ylene, thiophen-(2,4-, 2,5- or 3,4-)ylene, pyrrol-(1,3-, 2,4-, 2,5- or 3,4-)ylene, thiazol-(2,4- or 2,5-)ylene, imidazol-(1,4-, 2,4- or 2,5-)ylene, thiadiazol-2,5-ylene or their partially or completely reduced derivatives (e.g. (2,3- or 4,5-)dihydropyrrol-( 2,4-, 2,5- or 3,4-)ylene, 2,3,4,5 -tetrahydropyrrol-(2,4-, 2,5- or 3,4-)ylene).

And, examples of the 6-membered divalent cyclic group include phenyl-(1,3- or 1,4)ylene, cyclohexan-(1,3- or 1,4-)ylene, cyclohexen-(1,3-, 1,4-, 1,5-, 3,5- or 3,6-)ylene, 1,3-cyclohexadien-(1,3-, 1,4-, 1,5-, 2,4-, 2,5- or 2,6-)ylene, 1,4-cyclohexadien-(1,3-, 1,4- or 1,5-)ylene, pyridin-(2,4-, 2,5-, 2,6- or 3,6-)ylene, pyran-(2,4-, 2,5-, 2,6-, 3,5-, 3,6- or 4,6-)ylene, pyrazin-(2,5- or 2,6-)ylene, pyrimidin-(2,4- or 2,5-)ylene, pyridazin-3,5-ylene or their partially or completely reduced derivatives (e.g. piperidin-(2,4-, 2,5-, 2,6- or 3,6-)ylene, piperazin-(2,5- or 2,6-)ylene). Among them, phenyl-1,4-ylene and thiophen-2,5-ylene, etc. are especially preferable.

Preferable chain groups in an optionally substituted divalent chain group shown by B include a divalent $C_{2-4}$ chain-like hydrocarbon groups such as ethylene, ethenylene, ethynylene, trimethylene, propenylene, propynylene, propadienylene, tetramethylene, butenylene, butynylene or butanedienylene, etc.

Divalent cyclic or chain groups shown by B may have 1 or 2 substituents at any possible position. Examples of such substituents include $C_{1-3}$ alkyl groups (e.g. methyl, ethyl, propyl, isopropyl group), $C_{2-3}$ alkenyl groups (e.g. vinyl, 1-propenyl, allyl, allenyl group), $C_{2-3}$ alkynyl groups (ethynyl, 1-propynyl, propargyl group), $C_{3-6}$ cycloalkyl groups (e.g. cyclopropyl), halogen (e.g. chlorine, bromine, fluorine, iodine), hydroxyl, $C_{1-4}$ alkoxy groups (e.g. methoxy), di-$C_{1-4}$ alkylamino groups (e.g. dimethylamino), halogeno-$C_{1-4}$ alkyl groups (e.g. trifluoromethyl), oxo, $C_{1-3}$ acyl groups (e.g. formyl), $C_{1-3}$ alkoxy-$C_{1-3}$ alkyl groups (e.g. methoxymethyl, 2 -ethoxyethyl), etc.

Y can be a cyano group, carboxyl group, carbamoyl group, nitro group, hydroxyl group, amino group or a lower hydrocarbon group, for example, $C_{1-3}$ alkyl group (e.g. methyl, ethyl, propyl, iso-propyl group), $C_{2-3}$ alkenyl group (e.g. vinyl, 1-methylvinyl, 1-propenyl, allyl, allenyl group), $C_{2-3}$ alkynyl group (e.g. ethynyl, 1-propinyl, propargyl group) and $C_{3-6}$ cycloalkyl group (e.g. cyclopropyl group), etc., aryl group, preferably $C_{6-10}$ aryl group such as phenyl group, naphthyl group; 5- or 6-membered heterocyclic group containing 1 to 3 hetero atoms selected from nitrogen, oxygen and sulfur atom such as pyrrolyl, imidazolyl, pyrazolyl, thienyl, furyl, thiazolyl, thiadiazolyl, oxazolyl, oxadiazolyl, pyridyl, pyranyl, pyrazinyl, pyrimidinyl, pyridazinyl or their partially or completely reduced derivatives (e.g. 2,3,4,5 -tetrahydropyrrolyl, (1,2,3,4-, 1,2,5,6- or 3,4,5,6 -)tetrahydropyridyl), dioxoranyl, piperidino, morpholino, N-methylpiperazinyl, N-ethylpiperazinyl, dioxanyl, etc.

When Y is a lower hydrocarbon group, aryl group or a 5- or 6-membered heterocyclic group, it may have 1 or 2 substituents. Examples of such substituents include a $C_{1-3}$ alkyl group (e.g. methyl, ethyl propyl, iso-propyl group), $C_{2-3}$ alkenyl group (e.g. vinyl, 1 -methylvinyl, 1-propenyl, allyl, allenyl group), $C_{2-3}$ alkynyl group (ethynyl, 1-propinyl, propargyl group) or $C_{3-6}$ cycloalkyl group (e.g. cyclopropyl group), and, besides, halogen (e.g. fluorine), hydroxyl, oxo, a $C_{1-4}$ alkoxy group (e.g. methoxy), di-$C_{1-4}$ alkylamino group (e.g. dimethylamino, diethylamino), halogeno-$C_{1-4}$ trifluoromethyl), $C_{1-3}$ acyl (e.g. formyl), hydroxy-$C_{1-4}$ alkyl (e.g. hydroxymethyl, 2-hydroxyethyl), $C_{1-4}$ alkoxy-$C_{1-4}$ alkyl e.g. methoxymethyl, 2-ethoxyethyl), etc.

Examples of a halogen atom shown by Y include fluorine, chlorine, bromine or iodine. Y may be an alkoxy group, alkylthio group, alkanoylamino group or alkanoyloxy group, and, as the alkyl portion of these groups, mention is made of those optionally substituted as exemplified in the case where Y is a lower hydrocarbon group. Y may be an aryloxy group, arylthio group, aroylamino group or aroyloxy group, and, as the aryl portion of these groups, mention is made of those optionally substituted as exemplified in the case where Y is an aryl group. Further, Y may be a heterocyclicoxy group, heterocyclic-thio group, heterocycliccarbonylamino group or heterocyclic-carbonyloxy group, and, as the heterocyclic portion of these groups, mention is made of groups optionally substituted as exemplified in the case where Y is a 5- to 6-membered heterocyclic group. Y may be a substituted amino group such as a mono-substituted or di-substituted amino group, and, as the substituent of the substituted amino group, mention is made of the above-mentioned lower hydrocarbon groups, aryl group and 5- to 6-membered heterocyclic groups.

In the straight-chain divalent group having 2 to 5 atoms shown by Z, which is constituted of optionally substituted carbon atoms or constituted of optionally substituted carbon atoms and one optionally substituted hetero-atom (nitrogen atom, oxygen atom or sulfur atom), examples of the group constituted of carbon atoms include $C_{2-5}$ alkylene groups such as ethylene, trimethylene, tetramethylene, pentamethylene, etc., $C_{2-5}$ alkenylene groups such as vinylene, propenylene, 1- or 2-butenylene, butadienylene, 1- or 2-pentenylene, 1,3- or 1,4-pentadienylene, etc. and $C_{2-5}$ alkynylene groups such as ethynylene, 1- or 2-propynylene, 1- or 2 -butynylene, 1-, 2- or 3-pentynylene, etc.

As the group constituted of optionally substituted carbon atoms and one optionally substituted hetero-atom (nitrogen atom, oxygen atom or sulfur atom), mention is made of a group shown by —$Z^1$—$Z^2$—$Z^3$— wherein $Z^1$ and $Z^3$ independently stand for a bonding hand or an optionally substituted divalent lower hydrocarbon group, and $Z^2$ stands for —O—, a group shown by the formula: —S(O)p— wherein p denotes an integer of 0 to 2, or a group of the formula: —$NR^3$— wherein $R^3$ stands for hydrogen atom or an optionally substituted lower hydrocarbon group. Examples of the divalent lower hydrocarbon group shown by $Z^1$ and $Z^3$ include $C_{1-4}$ alkylene groups such as methylene, ethylene, trimethylene, tetramethylene, etc., $C_{2-4}$ alkenylene groups such as vinylene, propenylene, 1- or 2-butenylene, butadienylene, etc., and $C_{2-4}$ alkynylene groups such as ethynylene, 1- or 2 -propynylene, 1- or 2-butynylene, etc.

Examples of the lower hydrocarbon group shown by $R^3$ include $C_{1-3}$ alkyl groups (e.g. methyl, ethyl, propyl, iso-propyl group), $C_{2-3}$ alkenyl groups (e.g. vinyl, 1-methylvinyl, 1-propenyl, ally, allenyl group), $C_{2-3}$ alkynyl groups (e.g. ethynyl, 1-propynyl, propargyl group) and $C_{3-6}$ cycloalkyl (e.g. cyclopropyl group), etc. The straight-chain divalent group having 2 to 5 atoms constituted of carbon atoms of Z, the divalent lower hydrocarbon group of $Z^1$ and $Z^3$ and the lower hydrocarbon group of $R^3$ may have one or two substituents, and examples of such substituents include a $C_{1-3}$ alkyl group (e.g. methyl, ethyl propyl, iso-propyl group), $C_{2-3}$ alkenyl group (e.g. vinyl, 1-methylvinyl, 1-propenyl, allyl, allenyl group), $C_{2-3}$ alkynyl group (e.g. ethynyl, 1-propinyl, propargyl group), $C_{3-6}$ cycloalkyl group (e.g. cyclopropyl group), and, besides, halogen (e.g. fluorine), hydroxyl, oxo, a $C_{1-3}$ alkoxy group (e.g. methoxy), di-$C_{1-3}$ alkyl-amino group (e.g. dimethylamino, diethylamino), halogeno-$C_{1-3}$ alkyl group (e.g. trifluoromethyl), $C_{1-3}$ acyl (e.g. formyl), hydroxy-$C_{1-3}$ alkyl group (e.g. hydroxymethyl, 2 -hydroxyethyl), $C_{1-3}$ alkoxy-$C_{1-3}$ alkyl group (e.g. methoxymethyl, 2-ethoxyethyl), etc.

In a preferable compound (IV) of the present invention, as an optionally hydrogenated pyrrole ring shown by A, mention is made of a pyrrole ring and pyrroline ring, and, as a lower alkyl group shown by R, mention is made of $C_{1-3}$ alkyl groups (e.g. methyl, ethyl, propyl, iso-propyl group).

Examples of optionally esterified carboxyl groups shown by —$COOR^1$ and —$COOR^2$ include carboxyl groups optionally esterified with, among others, a $C_{1-5}$ lower alkyl group (e.g. methyl, ethyl, propyl, iso-propyl, n-butyl, iso-butyl, sec-butyl, tert-butyl, n-pentyl, iso-pentyl, sec-pentyl, neo-pentyl, tert-pentyl group, etc.), an optionally substituted benzyl group, preferably benzyl group which may be substituted with nitro or a $C_{1-4}$ alkoxy group (e.g. benzyl, nitrobenzyl, methoxybenzyl group, etc.) or an optionally substituted phenyl group, preferably phenyl group which may be substituted with nitro or a $C_{1-4}$ alkoxy group (e.g. phenyl, nitrophenyl, methoxyphenyl group, etc.).

m denotes an integer of 2 to 4, preferably 3, n denotes an integer of 2 to 6, preferably 2 to 4, respectively, and $R^1$ may be different in each of n repeating units, and R may be different in each of m repeating units, respectively.

Typical examples of the compounds (I) of the present invention include

1) [N-[4-[2-(2-amino-4-hydroxy-7-methylpyrrolo[2,3-d]pyrimidin-5-yl)ethyl]benzoyl]-γ-L-glutamyl]-L-glutamic acid, 2) [N-[4-[3-(2-amino-4-hydroxy-7-methylpyrrolo[2,3-d]pyrimidin-5-yl)propyl]benzoyl]-γ-L-glutamyl]-L-glutamic acid, 3) [N-[5-[2-(2-amino-4-hydroxy-7-methylpyrrolo[2,3-d]pyrimidin-5-yl)ethyl]-2-thenoyl]-γ-L-glutamyl]-L-glutamic acid, 4) [N-[5-[3-(2-amino-4-hydroxy-7-methylpyrrolo[2,3-d]pyrimidin-5-yl)propyl]-2-thenoyl]-γ-L-glutamyl]-L-glutamic acid, 5) [N-[4-[N-(2-amino-4-hydroxy-7-methylpyrrolo[2,3-d]pyrimidin-5-yl)methylamino]benzoyl]-γ-L-glutamyl]-L-glutamic acid, 6) [N-[4-[N-2-(2-amino-4-hydroxy-7-methylpyrrolo[2,3-d]pyrimidin-5-yl)ethylamino]benzoyl]-γ-L-glutamyl]-L-glutamic acid,
7) [N-[4-[N-[(2-amino-4-hydroxy-7-methylpyrrolo[2,3-d]pyrimidin-5-yl)methyl]-N-methylamino]benzoyl]-γ-L-glutamyl]-L-glutamic acid,
8) [N-[4-[N-[2-(2-amino-4-hydroxy-7-methylpyrrolo[2,3-d]pyrimidin-5-yl)ethyl]-N-methylamino]benzoyl]-γ-L-glutamyl]-L-glutamic acid,
9) [N-[4-[N-[(2-amino-4-hydroxy-7-methylpyrrolo[2,3-d]pyrimidin-5-yl)methyl]-N-propargylamino]benzoyl]-γ-L-glutamyl]-L-glutamic acid,
10) [N-[4-[N-[2-(2-amino-4-hydroxy-7-methylpyrrolo[2,3-d]pyrimidin-5-yl)ethyl]-N-propargylamino]benzoyl]-γ-L-glutamyl]-L-glutamic acid,
11) [N-[5-[N-(2-amino-4-hydroxy-7-methylpyrrolo[2,3-d]pyrimidin-5-yl)methylamino]-2-thenoyl]-γ-L-glutamyl]-L-glutamic acid,
12) [N-[5-[N-2-(2-amino-4-hydroxy-7-methylpyrrolo[2,3-d]pyrimidin-5-yl)ethylamino]-2-thenoyl]-γ-L-glutamyl]-L-glutamic acid,
13) [N-[5-[N-[(2-amino-4-hydroxy-7-methylpyrrolo[2,3-d]pyrimidin-5-yl)methyl]-N-methylamino]-2-thenoyl]-γ-L-glutamyl]-L-glutamic acid,
14) [N-[5-[N-[2-(2-amino-4-hydroxy-7-methylpyrrolo[2,3-d]pyrimidin-5-yl)ethyl]-N-methylamino]-2-thenoyl]-γ-L-glutamyl]-L-glutamic acid,
15) [N-[5-[N-[(2-amino-4-hydroxy-7-methylpyrrolo[2,3-d]pyrimidin-5-yl)methyl]-N-propargylamino]-2-thenoyl]-γ-L-glutamyl]-L-glutamic acid,
16) [N-[5-[N-[2-(2-amino-4-hydroxy-7-methylpyrrolo[2,3-d]pyrimidin-5-yl)ethyl]-N-propargylamino]-2-thenoyl]-γ-L-glutamyl]-L-glutamic acid,
17) [N-[4-[2-(2-amino-4-hydroxy-7-methylpyrrolo[2,3-d]pyrimidin-6-yl)ethyl]benzoyl]-γ-L-glutamyl]-L-glutamic acid,
18) [N-[4-[3-(2-amino-4-hydroxy-7-methylpyrrolo[2,3-d]pyrimidin-6-yl)propyl]benzoyl]-γ-L-glutamyl]-L-glutamic acid,
19) [N-[5-[2-(2-amino-4-hydroxy-7-methylpyrrolo[2,3-d]pyrimidin-6-yl)ethyl]-2-thenoyl]-γ-L-glutamyl]-L-glutamic acid,
20) [N-[5-[3-(2-amino-4-hydroxy-7-methylpyrrolo[2,3-d]pyrimidin-6-yl)propyl]-2-thenoyl]-γ-L-glutamyl]-L-glutamic acid,
21) [N-[4-[N-[(2-amino-4-hydroxy-7-methylpyrrolo[2,3-d]pyrimidin-6-yl)methyl]-N-methylamino]benzoyl]-γ-L-glutamyl]-L-glutamic acid,
22) [N-[4-[N-2-(2-amino-4-hydroxy-7-methylpyrrolo[2,3-d]pyrimidin-6-yl)ethyl]-N-methylamino]benzoyl]-γ-L-glutamyl]-L-glutamic acid,
23) [N-[5-[N-[(2-amino-4-hydroxy-7-methylpyrrolo[2,3-d]pyrimidin-6-yl)methyl]-N-methylamino]-2-thenoyl]-γ-L-glutamyl]-L-glutamic acid,
24) [N-[5-[N-[2-(2-amino-4-hydroxy-7-methylpyrrolo[2,3-d]pyrimidin-6-yl)ethyl]-N-methylamino]-2-thenoyl]-γ-L-glutamyl]-L-glutamic acid,
25) [N-[4-[2-(2-amino-4-hydroxycyclopentapyrimidin-5-yl)ethyl]benzoyl]-γ-L-glutamyl]-L-glutamic acid,
26) [N-[4-[3-(2-amino-4-hydroxycyclopentapyrimidin-5-yl)propyl]benzoyl]-γ-L-glutamyl]-L-glutamic acid,
27) [N-[4-[2-(2,4-diamino-7H-pyrrolo[2,3-d]benzimidin-5-yl)ethyl]benzoyl]-γ-L-glutamyl]-L-glutamic acid,
28) [N-[4-[2-(2,4-diamino-6,7-dihydro-5H-pyrrolo[2,3-d]pyrimidin-5-yl)ethyl]benzoyl]-γ-L-glutamyl]-L-glutamic acid,
29) [N-[4-[3-(2,4-diamino-6,7-dihydro-5H-pyrrolo[2,3-d]pyrimidin-5-yl)propyl]benzoyl]-γ-L-glutamyl]-L-glutamic acid,
30) [N-[4-[3-(2,4-diamino-7H-pyrrolo[2,3-d]pyrimidin-5-yl)-1-methylpropyl]benzoyl]-γ-L-glutamyl]-L-glutamic acid,
31) [N-[4-[3-(2,4-diamino-6,7-dihydro-5H-pyrrolo[2,3-d]pyrimidin-5-yl)-1-methylpropyl]benzoyl]-γ-L-glutamyl]-L-glutamic acid,
32) [N-[4-[2-(2,4-diamino-7H-pyrrolo[2,3-d]pyrimidin-5-yl)ethyl]-3-chlorobenzoyl]-γ-L-glutamyl]-L-glutamic acid,
33) [N-[4-[2-(2-amino-4-hydroxy-7H-pyrrolo[2,3-d]pyrimidin-5-yl)ethyl]-3-chlorobenzoyl]-γ-L-glutamyl]-L-glutamic acid,
34) [N-[4-[3-(2,4-diamino-7H-pyrrolo[2,3-d]pyrimidin-5-yl)propyl]-3-chlorobenzoyl]-γ-L-glutamyl]-L-glutamic acid,
35) [N-[5-[2-(2,4-diamino-7H-pyrrolo[2,3-d]pyrimidin-5-yl)ethyl]-2-thenoyl]-γ-L-glutamyl]-L-glutamic acid,
36) [N-[5-[2-(2-amino-4-hydroxy-7H-pyrrolo[2,3-d]pyrimidin-5-yl)ethyl]-2-thenoyl]-γ-L-glutamyl]-L-glutamic acid,
37) [N-[4-[N-2-(2,4-diamino-7H-pyrrolo[2,3-d]pyrimidin-5-yl)ethylamino]benzoyl]-γ-L-glutamyl]-L-glutamic acid,
38) [N-[4-[N-2-(2,4-diamino-6,7-dihydro-5H-pyrrolo[2,3-d]pyrimidin-5-yl)ethylamino]benzoyl]-γ-L-glutamyl]-L-glutamic acid,
39) [N-[4-[N-[2-(2,4-diamino-5H-pyrrolo[2,3-d]pyrimidin-5-yl)ethyl]-N-methylamino]benzoyl]-γ-L-glutamyl]-L-glutamic acid,
40) [N-[4-[N-[2-(2,4-diamino-5H-pyrrolo[2,3-d]pyrimidin-5-yl)ethyl]-N-(tert-butoxycarbonyl)amino]benzoyl]-γ-L-glutamyl]-L-glutamic acid,
41) [N-[4-[2-(2,4-diamino-7H-pyrrolo[2,3-d]pyrimidin-6-yl)ethyl]benzoyl]-γ-L-glutamyl]-L-glutamic acid,
42) [N-[4-[2-(2,4-diamino-6,7-dihydro-5H-pyrrolo[2,3-d]pyrimidin-6-yl)ethyl]benzoyl]-γ-L-glutamyl]-L-glutamic acid,
43) [N-[4-[3-(2,4-diamino-7H-pyrrolo[2,3-d]pyrimidin-6-yl)propyl]benzoyl]-γ-L-glutamyl]-L-glutamic acid,
44) [N-[4-[3-(2,4-diamino-6,7-dihydro-5H-pyrrolo[2,3-d]pyrimidin-6-yl)propyl]benzoyl]-γ-L-glutamyl]-L-glutamic acid,
45) [N-[4-[2-(2-amino-4-hydroxy-7H-pyrrolo[2,3-d]pyrimidin-5-yl)ethyl]benzoyl]-γ-L-glutamyl]-L-glutamic acid,
46) [N-[4-[2-(2-amino-4-hydroxy-6,7-dihydro-5H-pyrrolo[2,3-d]pyrimidin-5-yl)ethyl]benzoyl]-γ-L-glutamyl]-L-glutamic acid,
47) [N-[4-[3-(2-amino-4-hydroxy-6,7-dihydro-5H-pyrrolo[2,3-d]pyrimidin-5-yl)propyl]benzoyl]-γ-L-glutamyl]-L-glutamic acid,
48) [N-[4-[2-(2-amino-4-hydroxy-7H-pyrrolo[2,3-d]pyrimidin-6-yl)ethyl]benzoyl]-γ-L-glutamyl]-L-glutamic acid,
49) [N-[4-[2-(2-amino-4-hydroxy-6,7-dihydro-5H-pyrrolo[2,3-d]pyrimidin-6-yl)ethyl]benzoyl]-γ-L-glutamyl]-L-glutamic acid,
50) [N-[4-[3-(2-amino-4-hydroxy-7H-pyrrolo[2,3-d]pyrimidin-6-yl)propyl]benzoyl]-γ-L-glutamyl]-L-glutamic acid,
51) [N-[4-[3-(2-amino-4-hydroxy-6,7-dihydro-5H-pyrrolo[2,3-d]pyrimidin-6-yl)propyl]benzoyl]-γ-L-glutamyl]-L-glutamic acid,
52) [N-[4-[2-(2,4-diamino-furo[2,3-d]pyrimidin-5-yl)ethyl]benzoyl]-γ-glutamyl]-L-glutamic acid,
53) [N-[4-[2-(2-amino-4-hydroxyfuro[2,3-d]pyrimidin-5-yl)ethyl]benzoyl]-γ-L-glutamyl]-L-glutamic acid,
54) [N-[4-[3-(2,4-diaminofuro[2,3-d]pyrimidin-5-yl)propyl]benzoyl]-γ-L-glutamyl]-L-glutamic acid, 55) [N-[4-[3-(2-amino-4-hydroxyfuro[2,3-d]pyrimidin-5-yl)propyl]benzoyl]-γ-L-glutamyl]-L-glutamic acid,
56) [N-[4-[2-(2,4-diaminothieno[2,3-d]pyrimidin-5-yl)ethyl]benzoyl]-γ-L-glutamyl]-L-glutamic acid,
57) [N-[4-[2-(2-amino-4-hydroxythieno[2,3-d]pyrimidin-5-yl)ethyl]benzoyl]-γ-L-glutamyl]-L-glutamic acid,
58) [N-[5-[2-(2,4-diaminothieno[2,3-d]pyrimidin-5-yl)ethyl]-2-thenoyl]-γ-L-glutamyl]-L-glutamic acid,
59) [N-[5-[2-(2-amino-4-hydroxythieno[2,3-d]pyrimidin-5-yl)ethyl]-2-thenoyl]-γ-L-glutamyl]-L-glutamic acid,
60) [N-[4-[3-(2,4-diaminothieno[2,3-d]pyrimidin-5-yl)propyl]benzoyl]-γ-L-glutamyl]-L-glutamic acid,
61) [N-[4-[3-(2-amino-4-hydroxythieno[2,3-d]pyrimidin-5-yl)propyl]benzoyl]-γ-L-glutamyl]-L-glutamic acid,
62) [N-[5-[3-(2,4-diaminothieno[2,3-d]pyrimidin-5-yl)propyl]-2-thenoyl]-γ-L-glutamyl]-L-glutamic acid,
63) [N-[5-[3-(2-amino-4-hydroxythieno[2,3-d]pyrimidin-5-yl)propyl]-2-thenoyl]-γ-L-glutamyl]-L-glutamic acid,
64) [N-[4-[2-(2,4-diamino-6,7-dihydro-5H-pyrrolo[2,3-d]pyrimidin-5-yl)ethylthio]benzoyl]-γ-L-glutamyl]-L-glutamic acid,
65) [N-[4-[3-(2-amino-4-hydroxy-7H-pyrrolo[2,3-d]pyrimidin-5-yl)propyl]benzoyl]-γ-L-glutamyl]-L-glutamic acid,
66) [N-[4-[N-[2-(2,4-diamino-6,7-dihydro-5H-pyrrolo[2,3-d]pyrimidin-5-yl)ethyl] aminobenzoyl]-γ-L-glutamyl]-L-glutamic acid,
67) [N-[5-[3-(2,4-diamino-7H-pyrrolo[2,3-d]pyrimidin-5-yl)propyl]-2-thenoyl]-γ-L-glutamyl]-L-glutamic acid,
68) [N-[4-[N-2-(2-amino-4-hydroxy-7H-pyrrolo[2,3-d]pyrimidin-5-yl)ethylamino]benzoyl]-γ-L-glutamyl]-L-glutamic acid,
69) [N-[4-[N-[2-(2-amino-4-hydroxy-7H-pyrrolo[2,3-d]pyrimidin-5-yl)ethyl]-N-methylamino]benzoyl]-γ-L-glutamyl]-L-glutamic acid,
70) [N-[4-[N-[2-(2-amino-4-hydroxy-7H-pyrrolo[2,3-d]pyrimidin-5-yl)ethyl]-N-propargylamino]benzoyl]-γ-L-glutamyl]-L-glutamic acid,
71) [N-[5-[N-2-(2-amino-4-hydroxy-7H-pyrrolo[2,3-d]pyrimidin-5-yl)ethylamino]-2-thenoyl]-γ-L-glutamyl]-L-glutamic acid,
72) [N-[5-[N-[2-(2-amino-4-hydroxy-7H-pyrrolo[2,3-d]pyrimidin-5-yl)ethyl]-N-methylamino]-2-thenoyl]-γ-L-glutamyl]-L-glutamic acid,
73) [N-[5-[N-[2-(2-amino-4-hydroxy-7H-pyrrolo[2,3-d]pyrimidin-5-yl)ethyl-N-propargylamino]-2-thenoyl]-γ-L-glutamyl]-L-glutamic acid,
74) [N-[4-[N-(2-amino-4-hydroxythieno[2,3-d]pyrimidin-5-yl)methylamino]benzoyl]-γ-L-glutamyl]-L-glutamic acid,
75) [N-[4-[N-[(2-amino-4-hydroxythieno[2,3-d]pyrimidin-5-yl)methyl]-N-methylamino]benzoyl]-γ-L-glutamyl]-L-glutamic acid,
76) [N-[4-[N-[(2-amino-4-hydroxythieno[2,3-d]pyrimidin-5-yl)methyl]-N-propargylamino]benzoyl]-γ-L-glutamyl]-L-glutamic acid,
77) [N-[5-[N-(2-amino-4-hydroxythieno[2,3-d]pyrimidin-5-yl)methylamino]-2-thenoyl]-γ-L-glutamyl]-L-glutamic acid,
78) [N-[5-[N-[(2-amino-4-hydroxythieno[2,3-d]pyrimidin-5-yl)methyl]-N-methylamino]-2-thenoyl]-γ-L-glutamyl]-L-glutamic acid,
79) [N-[5-[N-[(2-amino-4-hydroxythieno[2,3-d]pyrimidin-5-yl)methyl]-N-propargylamino]-2-thenoyl]-γ-L-glutamyl]-L-glutamic acid,
80) [N-[4-[N-[2-(2-amino-4-hydroxy-7H-pyrrolo[2,3-d]pyrimidin-5-yl)ethyl]-N-methylamino]-2-fluorobenzoyl]-γ-L-glutamyl]-L-glutamic acid,
81) [N-[4-[N-[2-(2-amino-4-hydroxy-7H-pyrrolo[2,3-d]pyrimidin-5-yl)ethyl]-N-methylamino]-2-fluorobenzoyl]-γ-L-glutamyl-L-glutamic acid,
82) [N-[4-[N-[2-(2-amino-4-hydroxy-7H-pyrrolo[2,3-d]pyrimidin-5-yl)ethyl]-N-propargylamino]-2-fluorobenzoyl]-γ-L-glutamyl]-L-glutamic acid,
83) [N-[4-[N-[2-(2-amino-4-hydroxy-7H-pyrrolo[2,3-d]pyrimidin-5-yl)ethyl]-N-propargylamino]-2-fluorobenzoyl]-γ-L-glutamyl-γ-L-glutamyl-L-glutamic acid,
84) [N-[4-[N-[2-(2-amino-4-hydroxy-7H-pyrrolo[2,3-d]pyrimidin-5-yl)ethyl]-N-propargylamino]-2-chlorobenzoyl]-γ-L-glutamyl]-L-glutamic acid,
85) [N-[4-[N-[2-(2-amino-4-hydroxy-7H-pyrrolo[2,3-d]pyrimidin-5-yl)ethyl]-N-propargylamino]-2-chlorobenzoyl]-γ-L-glutamyl-L-glutamyl-L-glutamic acid,
86) [N-[5-[N-[2-(2-amino-4-hydroxy-7H-pyrrolo[2,3-d]pyrimidin-5-yl)ethyl]-N-methylamino] thiazol-2-ylcarbonyl]-γ-L-glutamyl]-L-glutamic acid,
87) [N-[5-[N-[2-(2-amino-4-hydroxy-7H-pyrrolo[2,3-d]pyrimidin-5-yl)ethyl]-N-methylamino] thiazol-2-ylcarbonyl]-γ-L-glutamyl-L-glutamyl-L-glutamic acid,
88) [N-[5-[N-[2-(2-amino-4-hydroxy-7H-pyrrolo[2,3-d]pyrimidin-5-yl)ethyl]-N-methylamino]pyridin-2-ylcarbonyl]-γ-L-glutamyl]-L-glutamic acid,
89) [N-[5-[N-[2-(2-amino-4-hydroxy-7H-pyrrolo[2,3-d]pyrimidin-5-yl)ethyl]-N-methylamino]pyridin-2-ylcarbonyl]-γ-L-glutamyl-L-glutamyl-L-glutamic acid,
90) [N-[5-[N-[2-(2-amino-4-hydroxy-7H-pyrrolo[2,3-d]pyrimidin-5-yl)ethyl]-N-propargylamino]thiazol-2-ylcarbonyl]-γ-L-glutamyl]-L-glutamic acid,
91) [N-[5-[N-[2-(2-amino-4-hydroxy-7H-pyrrolo[2,3-d]pyrimidin-5-yl)ethyl]-N-propargylamino]thiazol-2-ylcarbonyl]-γ-L-glutamyl-L-glutamyl-L-glutamic acid,
92) [N-[5-[N-[2-(2-amino-4-hydroxy-7H-pyrrolo[2,3-d]pyrimidin-5-yl)ethyl]-N-propargylamino]pyridin-2-ylcarbonyl]-γ-L-glutamyl]-L-glutamic acid,
93) [N-[5-[N-[2-(2-amino-4-hydroxy-7H-pyrrolo[2,3-d]pyrimidin-5-yl)ethyl]-N-propargylamino]pyridin-2-ylcarbonyl]-γ-L-glutamyl-L-glutamyl-L-glutamic acid,
94) [N-[4-[2-(4-hydroxy-2-methyl-7H-pyrrolo[2,3-d]pyrimidin-5-yl)ethyl]-2-chlorobenzoyl]-γ-L-glutamyl]-L-glutamic acid,
95) [N-[4-[2-(2-amino-4-hydroxy-7H-pyrrolo[2,3-d]pyrimidin-5-yl)ethyl]-2-chlorobenzoyl]-γ-L-glutamyl]-L-glutamyl-L-glutamic acid,
96) [N-[4-[2-(4-hydroxy-2-methyl-7H-pyrrolo[2,3-d]pyrimidin-5-yl)ethyl]-2-fluorobenzoyl]-γ-L-glutamyl]-L-glutamic acid,
97) [N-[4-[2-(4-hydroxy-2-methyl-7H-pyrrolo[2,3-d]pyrimidin-5-yl)ethyl]-2-fluorobenzoyl]-γ-L-glutamyl] -γ-L-glutamyl-L-glutamic acid,
98) [N-[4-[2-(4-hydroxy-2-methyl-7H-pyrrolo[2,3-d]pyrimidin-5-yl)ethyl]-3-fluorobenzoyl]-γ-L-glutamyl]-L-glutamic acid,
99) [N-[4-[2-(4-hydroxy-2-methyl-7H-pyrrolo[2,3-d]pyrimidin-5-yl)ethyl]-3-chlorobenzoyl]-γ-L-glutamyl] -γ-L-glutamyl-L-glutamic acid,
100) [N-[5-[2-(4-hydroxy-2-methyl-7H-pyrrolo[2,3-d]pyrimidin-5-yl)ethyl]-2-thenoyl]-γ-L-glutamyl]-L-glutamic acid,
101) [N-[5-[2-(4-hydroxy-2-methyl-7H-pyrrolo[2,3-d]pyrimidin-5-yl)ethyl]-2-thenoyl]-γ-L-glutamyl]-γ-L-glutamyl-L-glutamic acid,
102) [N-[5-[2-(4-hydroxy-2-methyl-7H-pyrrolo[2,3-d]pyrimidin-5-yl)ethyl]thiazol-2-ylcarbonyl]-γ-L-glutamyl]-L-glutamic acid,
103) [N-[5-[2-(4-hydroxy-2-methyl-7H-pyrrolo[2,3-d]pyrimidin-5-yl)ethyl]thiazol-2-ylcarbonyl]-γ-L-glutamyl-γ-L-glutamyl-L-glutamic acid, 104) [N-[5-[2-(4-hydroxy-2-methyl-7H-pyrrolo[2,3 -d]pyrimidin-5-yl)ethyl]pyridin-2-ylcarbonyl]-γ-L-glutamyl]-L-glutamic acid,
105) [N-[5-[2-(4-hydroxy-2-methyl-7H-pyrrolo[2,3 -d]pyrimidin-5-yl)ethyl]pyridin-2-ylcarbonyl]-γ-L-glutamyl]-γ-L-glutamyl-L-glutamic acid,
106) [N-[4-[2-(2-amino-4-hydroxy-7H-pyrrolo[2,3 -d]pyrimidin-5-yl)ethyl]-2-chlorobenzoyl]-γ-L-glutamyl] -L-glutamic acid,
107) [N-[4-[2-(2-amino-4-hydroxy-7H-pyrrolo[2,3 -d]pyrimidin-5-yl)ethyl]-2-chlorobenzoyl]-γ-L-glutamyl] -γ-L-glutamyl-L-glutamic acid,
108) [N-[4-[2-(2-amino-4-hydroxy-7H-pyrrolo[2,3 -d]pyrimidin-5-yl)ethyl]-2-fluorobenzoyl]-γ-L-glutamyl] -L-glutamic acid,
109) [N-[4-[2-(2-amino-4-hydroxy-7H-pyrrolo[2,3 -d]pyrimidin-5-yl)ethyl]-2-fluorobenzoyl]-γ-L-glutamyl] -γ-L-glutamyl-L-glutamic acid,
110) [N-[4-[2-(2-amino-4-hydroxy-7H-pyrrolo[2,3 -d]pyrimidin-5-yl)ethyl]-3-fluorobenzoyl]-γ-L-glutamyl] -L-glutamic acid,
111) [N-[4-[2-(2-amino -4-hydroxy-7H-pyrrolo[2,3 -d]pyrimidin-5-yl)ethyl]-3-fluorobenzoyl]-γ-L-glutamyl] -γ-L-glutamyl-L-glutamic acid,
112) [N-[5-[2-(2-amino -4-hydroxy-7H-pyrrolo[2,3 -d]pyrimidin-5-yl)ethyl]thiazol-2-ylcarbonyl]-γ-L-glutamyl]-L-glutamic acid,
113) [N-[5-[2-(2-amino-4-hydroxy-7H-pyrrolo[2,3 -d]pyrimidin-5-yl)ethyl]thiazol-2-ylcarbonyl]-γ-L-glutamyl]-γ-L-glutamyl- -L-glutamic acid,
114) [N-[5-[2-(2-amino-4-hydroxy-7H-pyrrolo[2,3 -d]pyrimidin-5-yl)ethyl]pyridin-2-ylcarbonyl]-γ-L-glutamyl]-L-glutamic acid,
115) [N-[5-[2-(2-amino-4-hydroxy-7H-pyrrolo[2,3 -d]pyrimidin-5-yl)ethyl]pyridin-2-ylcarbonyl]-γ-L-glutamyl]-γ-L-glutamyl-L-glutamic acid,
116) [N-[4-[2-(2,4-diamino-7H-pyrrolo[2,3 -d]pyrimidin-5-yl)ethyl]benzoyl]-γ-L-glutamyl]-γ -L-glutamyl-L-glutamic acid,
117) [N-[4-[2-(2,4-diamino-7H-pyrrolo[2,3 -d]pyrimidin-5-yl)ethyl]-3-chlorobenzoyl]-γ-L-glutamyl] -γ-L-glutamyl-L-glutamic acid,
118) [N-[4-[2-(2-amino-4-hydroxy-7H-pyrrolo[2,3 -d]pyrimidin-5-yl)ethyl]-3-chlorobenzoyl]-γ-L-glutamyl] -γ-L-glutamyl-L-glutamic acid,
119) [N-[5-[2-(2,4-diamino-7H-pyrrolo[2,3 -d]pyrimidin-5-yl)ethyl]-2-thenoyl]-γ-L-glutamyl]-γ -L-glutamyl-L-glutamic acid,
120) [N-[5-[2-(2-amino-4-hydroxy-7H-pyrrolo[2,3 -d]pyrimidin-5-yl)ethyl]-2-thenoyl]-γ-L-glutamyl]-γ -L-glutamyl-L-glutamic acid,
121) [N-[4-[2-(2-amino-4-hydroxy-7H-pyrrolo[2,3 -d]pyrimidin-5-yl)ethyl]benzoyl]-γ-L-glutamyl]-γ -L-glutamyl-L-glutamic acid,
122) [N-[4-[N-[2-(2-amino-4-hydroxy-7H-pyrrolo[2,3 -d]pyrimidin-5-yl)ethyl]-N-propargylamino]benzoyl]-γ-L-glutamyl]-γ-L-glutamyl-L-glutamic acid,
123) [N-[5-[N-[2-(2-amino-4-hydroxy-7H-pyrrolo[2,3 -d]pyrimidin-5-yl)ethyl]-N-methylamino]-2-thenoyl]-γ-L-glutamyl]-γ-L-glutamyl-L-glutamic acid,
124) [N-[5-[N-[2-(2-amino-4-hydroxy-7H-pyrrolo[2,3 -d]pyrimidin-5-yl)ethyl]-N-propargylamino]-2-thenoyl]-γ -L-glutamyl]-γ-L-glutamyl-L-glutamic acid,
125) [N-[4-[N-[2-(2-amino-4-hydroxy-7H-pyrrolo[2,3 -d]pyrimidin-5-yl)ethyl]-N-methylamino]-3 -fluorobenzoyl]-γ-L-glutamyl]-γ-L-glutamyl-L-glutamic acid,
126) [N-[4-[N-[2-(2-amino-4-hydroxy-7H-pyrrolo[2,3 -d]pyrimidin-5-yl)ethyl]-N-methylamino]-3 -fluorobenzoyl]-γ-L-glutamyl]-L-glutamic acid,
127) [N-[4-[N-[2-(2-amino-4-hydroxy-7H-pyrrolo[2,3 -d]pyrimidin-5-yl)ethyl]-N-propargylamino]-3 -fluorobenzoyl]-γ-L-glutamyl]-L-glutamic acid,
128) [N-[4-[N-[2-(2-amino-4-hydroxy-7H-pyrrolo[2,3 -d]pyrimidin-5-yl)ethyl]-N-propargylamino]-3 -fluorobenzoyl]-γ-L-glutamyl]-γ-L-glutamyl-L-glutamic acid,
129) [N-[4-[N-[2-(2-amino-4-hydroxy-7H-pyrrolo[2,3 -d]pyrimidin-5-yl)ethyl]-N-methylamino]-2 -chlorobenzoyl]-y -L-glutamyl]-L-glutamic acid,
130) [N-[4-[N-[2-(2-amino-4-hydroxy-7H-pyrrolo[2,3 -d]pyrimidin-5-yl)ethyl]-N-methylamino]-3 -chlorobenzoyl]-γ-L-glutamyl]-γ-L-glutamyl-L-glutamic acid,
131) [N-[4-[N-[2-(2-amino-4-hydroxy-7H-pyrrolo[2,3 -d]pyrimidin-5-yl)ethyl]-N-propargylamino]-3 -chlorobenzoyl]-γ-L-glutamyl]-L-glutamic acid,
132) [N-[4-[N-[2-(2-amino-4-hydroxy-7H-pyrrolo[2,3 -d]pyrimidin-5-yl)ethyl]-N-propargylamino]-3 -chlorobenzoyl]-γ-L-glutamyl]-γ-L-glutamyl-L-glutamic acid,
133) [N-[4-[N-[2-(2-amino-4-hydroxy-7H-pyrrolo[2,3 -d]pyrimidin-5-yl)ethyl]-N-methylamino]-3 -chlorobenzoyl]-γ-L-glutamyl]-L-glutamic acid,
134) [N-[4-[N-[2-(2-amino-4-hydroxy-7H-pyrrolo[2,3 -d]pyrimidin-5-yl)ethyl]-N-methylamino]-3 -chlorobenzoyl]-γ-L-glutamyl]-γ-L-glutamyl-L-glutamic acid, and all the triglutamate corresponding to the above examples of diglutamates.

In the following, the method for production of the compounds (I) of this invention is explained.

The compounds (I) or salts thereof can be obtained by acylation of oligoglutamic acid derivatives shown by the formula (III) with carboxylic acids shown by the formula (II) or its reactive derivatives at the carboxyl group. The acylation may be performed by, for example, acylation of the compound (III) with the compound (II) or a reactive derivative thereof in the presence of carbodiimide, diphenylphosphoryl azide or diethyl cyanophosphonate. Generally, about 1 to 20 mole equivalents, preferably about 1 to 5 mole equivalents of the compound (III) are used relative to the compound (II) or its reactive derivative. Generally, about 1 to 25 mole equivalents, preferably about 1 to 5 mole equivalents of carbodiimide, diphenylphosphoryl azide or diethyl cyanophosphonate are used relative to the compound (II) or its reactive derivative. While, as the carbodiimide, dicyclohexylcarbodiimide is preferable for practical use, other carbodiimides such as diphenylcarbodiimide, di-o-tolylcarbodiimide, di-p-tolylcarbodiimide, di-tert-butylcarbodiimide, 1-cyclohexyl-3-(2 -morpholinoethyl)carbodiimide, 1-cyclohexyl-3-(4 -diethylaminocyclohexyl)carbodiimide, 1-ethyl-3-(2 -diethylaminopropyl)carbodiimide and 1-ethyl-3-(3 -diethylaminopropyl)carbodiimide may be used.

The acylation is preferably performed in the presence of a suitable solvent, for example, water, alcohols (e.g. methanol, ethanol), ethers (e.g. dimethyl ether, diethyl ether, tetrahydrofuran, dioxane, monoglyme, diglyme), nitriles (e.g. acetonitrile), esters (e.g. ethyl acetate), halogenated hydrocarbon (e.g. dichloromethane, chloroform, carbon tetrachloride), aromatic hydrocarbon (e.g. benzene, toluene, xylene), acetone, nitromethane, pyridine, dimethylsulfoxide, dimethylformamide, hexamethylphosphoramide, sulfolane or a suitable mixture of these solvents. This reaction is allowed to proceed usually at a pH ranging from about 2 to 14, preferably from about 6 to 9, at a temperature ranging from −10° C. to around the boiling point of the solvent then used (up to about 100° C.), preferably at a temperature ranging from about 0° to 50° C. for about 1 to 100 hours, preferably for about 2 to 48 hours. The pH of the reaction mixture is adjusted, upon necessity, by the addition of an acid (e.g. hydrochloric acid, sulfuric acid, phosphoric acid, nitric acid, acetic acid), a base (e.g. sodium methylate, sodium ethylate, sodium hydroxide, potassium hydroxide, barium hydroxide, lithium hydroxide, sodium carbonate, potassium carbonate, barium carbonate, calcium carbonate, sodium hydrogencarbonate, trimethylamine, triethylamine, triethanolamine, pyridine) or a buffer solution (e.g. phosphate buffer, borate buffer, acetate buffer), etc.

The reaction can be allowed to proceed more advantageously by using a catalyst capable of promoting acylation. Examples of such catalysts include base catalysts and acid catalysts. The base catalysts include tertiary amines (e.g. aliphatic tertiary amines such as triethylamine; aromatic tertiary amines such as pyridine, α-, β- or γ-picoline, 2,6-lutidine, 4-dimethylaminopyridine, 4-(1-pyrrolidinyl)pyridine, dimethylaniline and diethylaniline), and such acid catalysts include Lewis acids [e.g. anhydrous zinc chloride, anhydrous aluminum chloride ($AlCl_3$), anhydrous ferric chloride, titanium tetrachloride ($TiCl_4$), tin tetrachloride ($SnCl_4$), antimony pentachloride, cobalt chloride, cupric chloride, boron trifluoride etherate, etc.]. Among the catalysts described above, 4-dimethylaminopyridine or 4-(1-pyrrolidinyl)pyridine is preferable in many cases. The suitable amount of the catalyst is such that is enough to promote the acylation, being generally about 0.01 to 10 mole equivalents, preferably about 0.1 to 1 mole equivalent relative to the compound (II) or its reactive derivative. The reactive derivatives of the compound (II) at the carboxyl group, which are to be employed for the acylation, include acid halides (e.g. fluoride, chloride, bromide, iodide), acid anhydrides (e.g. iodoacetic acid anhydride, isobutyric acid anhydride), mixed acid anhydrides with monoalkylcarbonic acid esters (e.g. monomethylcarbonic acid ester, monoethylcarbonic acid ester, monopropylcarbonic acid ester, mono-iso-propylcarbonic acid ester, monobutylcarbonic acid ester, mono-iso-butylcarbonic acid ester, mono-sec-butylcarbonic acid ester, mono-tert-butylcarbonic acid ester), active esters (e.g. cyanomethyl ester, carboethoxymethyl ester, methoxymethyl ester, phenyl ester, o-nitrophenyl ester, p-nitrophenyl ester, p-carbomethoxyphenyl ester, p-cyanophenyl ester, thiophenyl ester), acid azides, mixed acid anhydrides with phosphoric acid diesters (e.g. dimethyl phosphate, diethyl phosphate, dibenzylphosphate, diphenylphosphate), and mixed acid anhydrides with phosphorous acid diesters (e.g. dimethyl phosphite, diethyl phosphite, dibenzyl phosphite, diphenyl phosphite), of the carboxylic acid (II). For acylation with such a reactive derivative, the solvent, the catalyst and the reaction temperature are the same as for acylation in the presence of the carbodiimide, diphenylphosphoryl azide or diethyl cyanophosphonate described above.

For production of the compound (I-1) in which —$COOR^1$ and —$COOR^2$ in the formula (I) are carboxyl groups, or a salt thereof, it is preferable that the compound, in which —$COOR^1$ and —$COOR^2$ in the formula of the compound (III) are esterified carboxyl groups, is allowed to react with the compound (II) or its reactive derivative at the carboxyl group as mentioned above, followed by deesterification by per se known degradation or catalytic reduction.

Such degradation can be performed by hydrolysis under basic conditions (method A), hydrolysis under acid conditions (method B-1) or hydrolysis under acid and non-aqueous conditions (method B-2). Bases used in the method A include metal alkoxides such as sodium methoxide, sodium ethoxide, sodium butoxide and potassium butoxide, metal hydroxides such as sodium hydroxide, potassium hydroxide, lithium hydroxide, and barium hydroxide, and amines such as ammonia, triethylamine and pyridine. Acids used in the method B-1 include mineral acids such as hydrochloric acid, hydrobromic acid, sulfuric acid, nitric acid and phosphoric acid, and organic acids such as trifluoroacetic acid, trichloroacetic acid, methanesulfonic acid, benzenesulfonic acid, p-toluenesulfonic acid and camphorsulfonic acid. Acids usable in the method B-2 include mineral acids such as hydrogen chloride, hydrogen bromide, perchloric acid, sulfuric acid, nitric acid and phosphoric acid, organic acids such as trifluoroacetic acid, trichloroacetic acid, methanesulfonic acid, benzenesulfonic acid, p-toluenesulfonic acid and camphorsulfonic acid, and Lewis acids such as anhydrous zinc chloride, anhydrous aluminum chloride ($AlCl_3$), anhydrous ferric chloride, titanium tetrachloride ($TiCl_4$), tin tetrachloride ($SnCl_4$), antimony pentachloride, cobalt chloride, cupric chloride and boron trifluoride etherate. Degradation is performed in a suitable solvent at a temperature ranging from 0° C. to the boiling point of the solvent, preferably at 10° to 80° C., for 30 minutes to two days. The solvent usable for the reaction in the method A or the method B-1 may be water, methanol, ethanol, propanol, butanol, ethylene glycol, methoxyethanol, ethoxyethanol, tetrahydrofuran, dioxane, monoglyme, diglyme, pyridine, dimethylformamide, dimethyl sulfoxide, sulfolane, or a mixture of them; the solvents usable for the reaction in the method B-2 may be ethyl acetate, dimethyl ether, diethyl ether, tetrahydrofuran, dioxane, monoglyme, diglyme, dichloromethane, chloroform, carbon tetrachloride, acetonitrile, benzene, toluene, xylene, nitromethane, pyridine or a suitable mixture of them.

The catalytic reduction (method C) is performed in a suitable solvent at a temperature ranging from about −40° C. to the boiling point of the solvent used, preferably at about 0° to 50° C. The solvents usable include water, alcohols (e.g. methanol, ethanol, propanol, iso-propanol, butyl alcohol, sec-butyl alcohol, tert-butyl alcohol, ethylene glycol, methoxyethanol, ethoxyethanol), acetic acid esters (e.g. methyl acetate, ethyl acetate), ethers (e.g. dimethyl ether, diethyl ether, tetrahydrofuran, dioxane, monoglyme, diglyme), aromatic hydrocarbons (e.g. benzene, toluene, xylene), pyridine, dimethylformamide and a suitable mixture of them. Examples of catalysts for the catalytic reaction include palladium, platinum, rhodium and Raney's nickel. Addition of a trace amount of acetic acid, trifluoroacetic acid, hydrochloric acid or sulfuric acid sometimes serves to allow the reaction to proceed advantageously.

The method for production of the compound (I-1) or a salt thereof is selected according to the nature of —$COOR^1$ and —$COOR^2$ in the starting compound (III); when —$COOR^1$ and —$COOR^2$ in the compound (III) are carboxyl groups esterified with a methyl, ethyl, propyl, butyl, sec-butyl, phenyl or substituted phenyl group, the method A or the method B-1 is applied advantageously; when —$COOR^1$ and $COOR^2$ are carboxyl groups esterified with an iso-propyl or tert-butyl group, the method B-2 is applied advantageously; and when —$COOR^1$ and —$COOR^2$ are carboxyl groups esterified with a benzyl or a substituted benzyl group, the method B-1 or the method C is applied advantageously. When —$COOR^1$ and —$COOR^2$ are different from each other, the methods A, B-1, B-2 and C may be combined appropriately.

The starting compound (II) or its reactive derivative to be used in this reaction can be easily obtained by the method disclosed in EP-A-334636 or EP-A-438261, and the starting compound (III) can be easily obtained according to the method disclosed in the literature reference [J. P. Greenstein and M. Winits, Chemistry of the Amino Acids Vols. I to III, John Wiley & Sons, Inc., New York. London (1961)].

The application of protective groups of each functional group to be used upon necessity in the above respective production steps is known and described in detail in the following literature references. [J. F. W. McOmine, Protective Groups in Organic Chemistry, Plenum Press, London and New York (1973); Pine, Hendrikson, Hammond, Organic Chemistry, 4th edition, [I]–[II], Hirokawa Shoten (1982); and M. Fieser and L. Fieser, Reagents for Organic Synthesis Vols. 1 to 13, Wiley-Interscience, New York, London, Sydney and Toronto (1969–1988)].

The amino group, hydroxyl group or mercapto group shown by X in the compound [I] can be converted, upon necessity, into one another by a known substituent-converting reaction on the pyrimidine ring [Protein Nucleic Acid Enzyme Extra Issue, Chemical Synthesis of Nucleic Acids, Kyoritsu Shuppan (1968)].

The compound (I) of this invention may form salts. Salts of bases include salts of alkali metals, alkaline earth metals, non-toxic metals, ammonium and quaternary ammonium, such as sodium, potassium, lithium, calcium, magnesium, aluminum, zinc, ammonium, trimethyl ammonium, triethanol ammonium, pyridinium and substituted pyridinium. Salts of acids include salts of mineral acids such as hydrochloric acid, sulfuric acid, nitric acid, phosphoric acid and boric acid, and salts of organic acids such as oxalic acid, tartaric acid, acetic acid, trifluoroacetic acid, methanesulfonic acid, benzenesulfonic acid, p-toluenesulfonic acid and camphorsulfonic acid.

The compound (I) or its salt produced by the abovementioned method can be isolated from the reaction mixture by conventional means for separation, such as concentration, extraction with a solvent, chromatography and recrystallization.

The compounds (I) of this invention or their salts are stored efficiently in cells and have inhibitory action against one or more species of enzymes whose substrate is folic acid or its related compounds. Therefore, these compounds can be used for the therapy of, not only papillary carcinoma, leukemia, mastocarcinoma, derencephalo epidermal cancer, squamous cell carcinoma, small cell cancer of the lung and lymphatic sarcoma, which have so far been treated with MTX, but also other various tumors, singly or in combination with any other antitumor agent.

The compounds (I) and pharmaceutically acceptable salts thereof, when used as antitumor agents, can be administered to warm-blooded animals particularly mammals (e.g. human, monkey, dog, cat, rabbit, rat, mice, etc.) orally and non-orally as they are or in the forms of, for example, powder, granules, tablets, capsules, suppositories and injections, which are prepared according to conventional methods using pharmaceutically acceptable vehicles, excipients, and diluents. The dose varies according to the animals, diseases, symptoms, compounds and administration routes; for example, the daily dose is about 2.0 to 200 mg, preferably 1.0 to 200 mg, more preferably 2.5 to 50 mg in terms of the compound (I) or its salt of this invention per kg of body weight of a warm-blooded animal described above for oral administration, and about 0.5 to 100 mg/kg, preferably 1.0 to 100 mg/kg, more preferably 1.0 to 2.0 mg/kg for non-oral administration. Injections may be administered intramuscularly, intraperitoneally, subcutaneously or intravenously. By these administrations, therapy of tumors can be performed without significant toxicity.

The preparations described above are produced by per se known processes. The above-mentioned oral preparations, for example, tablets may be produced by suitable combination with a binder (e.g. hydroxypropylcellulose, hydroxypropylmethylcellulose, macrogol, etc.), a disintegrator (e.g. starch, calcium carboxylmethylcellulose, etc.) and a lubricant (e.g. magnesium stearate, talc, etc.).

The non-oral preparations, for example, injections may be produced by suitable combination with an isotonizing agent (e.g. glucose, D-sorbitol, D-mannitol, sodium chloride, etc.), an antiseptic (e.g. benzyl alcohol, chlorobutanol, methyl p-hydroxybenzoate, propyl p-hydroxybenzoate, etc.) and a buffer (e.g. phosphate buffer, sodium acetate buffer, etc.). A practical process of production of tablets comprises, for example, mixing about 1.0 to 50 mg of the compound (I) or a salt thereof of this invention, 100 to 500 mg of lactose, about 50 to 100 mg of corn starch and about 5 to 20 mg of hydroxypropylcellulose for preparation of one tablet by a conventional means, granulating, mixing with corn starch and magnesium stearate and tabletting, so that tablets each weighing about 100 to 500 mg with a diameter of about 3 to 10 mm are obtained. The tablets may be coated with a mixture of acetone and ethanol, the mixture containing hydroxypropylmethylcellulose phthalate (about 10 to 20 mg per tablet) and castor oil (0.5 to 2.0 mg per tablet) at a concentration of about 5 to 10%, to give enteric coated tablets. As a practical example for the preparation of an injection, about 2.0 to 50 mg of a sodium salt of the compound (I) of this invention for preparation of one ampoule may ① be dissolved in about 2 ml of physiological saline, sealing the resultant solution in an ampoule and sterilizing the ampoule at 110° C. for about 30 minutes or ② be dissolved in a solution of about 10 to 40 mg of mannitol or sorbitol, in about 2 ml of sterile distilled water, filling the solution into an ampoule and freeze-drying and sealing the ampoule, so that an injection can be prepared. For use of the freeze-dried compound for subcutaneous, intravenous or intramuscular injection, the ampoule is opened and the content is dissolved in, for example, physiological saline so that the concentration of the compound may be about 0.5 to 100 mg/ml, preferably 1.0 to 50 mg/ml, more preferably 1.0 to 20 mg/ml.

Experiments showing pharmacological effects of the compounds (I) or their salts in the present invention are given below.

The thymidylate acid synthase (TS) inhibiting action, the 5-aminoimidazole-4-carboxyamide ribonucleotide transformylase (AICARTF) inhibiting action and the Meth A fibrosarcoma cell growth inhibiting action in vitro, of the typical subject compounds in the present invention obtained in the Working Examples described below, were determined by the following methods.

Experiment 1

Determination of TS inhibiting action

A roughly refined fraction of TS was prepared from Meth A fibrosarcoma cells serially cultivated in vitro. For culturing the cells, Eagle's minimum essential medium containing 10% (v/v) bovine fetal serum [MEM; Nissui Pharmaceutical Co. Ltd.] was used. The cells in logarithmic growth were recovered and washed twice with a physiological aqueous saline solution buffered with phosphate, which was then suspended in 0.2M sucrose, 0.01M Tris.HCl buffer solution (pH 7.5). The cells were destroyed by ultrasonic wave, and the suspension was subjected to centrifugation (100,000×g), then the supernatant was collected. Using bovine γ-groblin as the standard protein, the protein concentration was measured by using a protein.dye reagent (Bio-Rad), so that the protein concentration was adjusted to 10 mg/ml.

Enzymic reaction was conducted by partially modifying the method described in Biochemistry 5, 3546 (1966). The composition of the reaction medium was as follows; 0.058% (v/v) formaldehyde, 6.78 mM sodium fluoride, 0.2 mM 2-mercapto ethanol, 6.24 mg/ml bovine serum albumin, 80 µM 2'-deoxyuridine-5'-1 phosphoric acid (dUMP), 80 µM tetrahydrofolic acid, 2 mg/ml roughly refined TS fraction and 0.173M Tris.HCl buffer solution (pH 7.5). To the reaction medium were added the compounds of various concentrations obtained in Working Examples. 540 KBg of [$^3$H] dUMP relative to 50 µl of the ultimate reaction medium was added, and the reaction was allowed to proceed for 1 hour at 37° C. in a 96-microwell plate. After completion of the reaction, 26.65% trichloroacetic acid and 3.33 mg/ml dUMP were added to suspend the reaction. To the reaction mixture was added 220 µl of 11.4 mg/ml activated charcoal. The whole mixture was subjected to centrifugation, and the radioactivity in 100 µl of the supernatant was measured by liquid scintillation counter to determine the concentration required for 50% inhibiting the TS activity ($ICa_{50}$), as shown in Table 1.

Experiment 2

Measurement of AICARTF inhibiting action

AICARTF was prepared from CCRF-CEM human lymphoblast leukemia cells by partially modifying the method described in Biochemistry 20 337 (1981), S. J. Benkovic, et al.

The enzymic reaction was conducted by adding the compounds of various concentrations in Working Examples to 0.95 ml of a solution consisting of a 32.5 µM Tris.HCl buffer solution (pH 7.4), 5 µM 2 -mercaptoethanol, 25 µM potassium chloride, 0.1 µM (−)-10 -formyl tetrahydrofolic acid and AICARTF, and, before starting the reaction, 0.05 ml of 1 mM 5-aminoimidazole-4-carboxylamide ribonucleotide.

The UV spectrum was measured at 298 nm for 15 minutes at the interval of 15 seconds to evaluate by the increase of absorbance due to the production of tetrahydrofolic acid to determine the concentration required for 50% inhibiting the activity of AICARTF ($IC_{50}$). The results are shown in Table 1.

TABLE 1

| Compound | TS | $IC_{50}$ (µM) AICARTF |
| --- | --- | --- |
| Ex. 6 | 36 | 9 |
| Ex. 7 | 40 | 6 |
| Ex. 8 | 21 | 0.6 |
| Ex. 9 | 20 | 0.4 |
| Ex. 10 | 20 | 0.2 |

Experiment 3

Measurement of inhibiting action against growth of Meth A fibrosarcoma (Meth A) cells Meth A cells ($2\times10^4$/ml) prepared by a conventional method were inoculated into each well of the 12-microwell plate (2.0 ml in a well), and subjected to standing culture at 37° C. under 5% $CO_2$. The compounds obtained in Working Examples dissolved at appropriate concentrations were diluted to 2–10 times stepwise with an MEM (Nissui Pharmaceutical Co., Ltd.) solution, to and the resulting dilutions were added to the culture medium. The medium was again subjected to standing culture at 37° C. under 5% $CO_2$ for 72 hours. Then, the total number of cells at each concentration was measured by Coulter counter (Coulter Electronic, Florida in U.S.A.), and the average value of the cells in three wells was expressed by the number of cells per milliliter.

The concentrations of the respective compounds required for decreasing the number of cells in the untreated control group by 50% was made $IC_{50}$ of the respective compounds. The results are shown in Table 2.

TABLE 2

| Compound | $IC_{50}$ (µM) |
| --- | --- |
| Ex. 6 | 0.61 |
| Ex. 7 | 0.58 |

EXAMPLES

The following Reference Examples and Working Examples will explain the present invention more concretely.

In the following reference and working examples, NMR spectrum was measured by means of Gemini 200 (200 MHz)-spectrometer, and all the δ values were shown by ppm. Symbols in the examples have the following meanings.

s: singlet d: doublet t: triplet

ABq: AB type quartet dd: double doublet dt: double triplet m: multiplet br.: broad J: coupling constant sh: shoulder Hz: hertz $CDCl_3$: dichloroform DMSO-$d_6$: dimethyl-sulfoxide $D_2O$: Deuterium Oxide (water-$d_2$)

room temperature: 10°–30° C.

%:% (w/w)

Reference Example 1

Production of methyl [N-(tert-butoxycarbonyl)-$O^1$ -methyl-γ-L-glutamyl]-γ-benzyl-L-glutamate N-(tert-butoxycarbonyl)-L-glutamic acid methyl dicyclohexylamine (10.04 g) was dispersed in a mixture of ethyl acetate (110 ml) and an aqueous solution of 2M sodium hydrogensulfate (44 ml). The dispersion was vigorously shaken in a separating funnel to give a solution. The aqueous layer was discarded, and the organic layer was washed with 2M sodium hydrogensulfate and a saturated aqueous saline solution, and was dried over anhydrous magnesium sulfate. The solvent was distilled off under reduced pressure. The residue and ethyl γ-benzyl-L-glutamate hydrochloride (7.18 g) were dissolved in dry dimethylformamide (50 ml). To the solution was added at 0° C. a solution of diethyl cyanophosphorate (4.07 g) in dry dimethylformamide (50 ml), and the mixture was stirred for 15 minutes. To the mixture was added dropwise a dry dimethylformamide solution (50 ml) of triethylamine (4.82 g), which was stirred for one hour at 0° C., then for 15 hours at room temperature. The reaction mixture was diluted with benzene (1000 ml) and ethyl acetate (2000 ml), which was washed with 5% hydrochloric acid, water, a saturated aqueous saline solution, a saturated aqueous solution of sodium hydrogencarbonate, water and a saturated aqueous saline solution, successively, then dried over anhydrous magnesium sulfate. The solvent was distilled off under reduced pressure. The residue was recrystallized from chloroform/petroleum ether to afford the above-titled compound (8.79 g).

Specific rotation: $[\alpha]D^{22}$-23.4 (c=1.0, MeOH) $^1$H-NMR (CDCl$_3$)δ: 1.44(9H,s), 1.82–2.33(6H,m), 2.40–2.58(2H,m), 3.73(6H,s), 4.20–4.37(1H,m), 4.61(1H,dt,J=7.6, 1.2 Hz), 5.21(2H,s), 5.20–5.33(1H,m), 6.46–6.60(1H,m), 7.36(5H,s) IR(KBr): 3350, 1740, 1680, 1640, 1520 cm$^{-1}$

Reference Example 2

Production of [N-(tert-butoxycarbonyl)-O$^1$-methyl-γ-L-glutamyl]-L-glutamic acid methyl dicyclohexylamine salt To a methanol solution (60 ml) of the compound obtained in Reference Example 1 (3.88 g) was added 10% palladium carbon (390 mg; manufactured by Engelhard Co., Ltd. in U.S.A.), and the mixture was stirred for 2.5 hours under hydrogen atmosphere. The catalyst was filtered off by using celite, then the filtrate was subjected to distillation under reduced pressure. The residue was dissolved in ether (50 ml), and the solution was cooled to 0° C., and there was added, while stirring, dicyclohexylamine (1.72 ml). The stirring was continued for 10 minutes, then precipitating crystals were collected by filtration and washed with ether to give the above-titled compound (3.97 g).

Specific rotation: $[\alpha]D^{20}$-17.8 (c=1.0, MeOH) IR(KBr): 3300, 2940, 2850, 1750, 1725, 1710, 1670, 1540 cm$^{-1}$

Reference Example 3

Production of [O$^1$-methyl-γ-L-glutamyl]-γ-benzyl-L-glutamic acid methyl hydrochloride To a dichloromethane (250 ml) solution of the compound of Reference Example 2 (3.88 g) was added trifluoroacetic acid (6.5 ml). The mixture was stirred for 4 hours at room temperature, then the solvent was distilled off under reduced pressure. The residue was dissolved in a mixture of water and dichloromethane (1:1, 100 ml). The solution was neutralized with a saturated aqueous solution of sodium hydrogenphosphate, then the organic layer was separated. The organic layer was washed with a saturated aqueous saline solution and dried over anhydrous magnesium sulfate. The solvent was distilled off under reduced pressure, and the residue was dissolved in ether (50 ml). To the solution was added a 0.4 mol. hydrochloric acid ether solution (30 ml). The resultant crystalline precipitate was collected by filtration and dried to give the above-titled compound (2.73 g).

Specific rotation: $[\alpha]D^{20}$+25.9 (c=1.0, MeOH) $^1$H-NMR (CDCl$_3$)δ: 1.95–2.70(8H,m), 3.67(3H,s), 3.75(3H,s), 4.19–4.22(1H,m), 4.43–4.58(1H,m), 5.09(2H,s), 7.73(5H,s), 7.64–7.79(1H,m)

Reference Example 4

Production of methyl [N-(tert-butoxycarbonyl)-O$^1$-methyl-γ-L-glutamyl]-[O$^1$-methyl-γ-L-glutamyl]-γ-benzyl-L-glutamate In substantially the same manner as Reference Example 1, the above-titled compound (1.61 g) was obtained from the compound of Reference Example 2 (1.75 g) and γ-benzyl-L-glutamic acid methyl hydrochloride (975 mg).

Specific rotation: $[\alpha]D^{21}$+31.1 (c=1.0, MeOH) $^1$H-NMR (CDCl$_3$): 1.44(9H,s), 1.70–1.55(12H,m), 3.73(9H,s), 4.22–4.36(1H,m), 4.50–4.65(2H,m), 5.12(2H,s), 5.29(1H,d, J=8.6 Hz), 6.67(1H,d,J=7.8 Hz), 6.80(1H,d,J=8.4 Hz), 7.35(5H,s) IR(KBr): 3310, 1740, 1680, 1645, 1535 cm$^{-1}$

Reference Example 5

Production of methyl [N-(tert-butoxycarbonyl)-O$^1$-methyl-γ-L-glutamyl]-[O$^1$-methyl-γ-L-glutamyl]-[O$^1$-methyl-γ-L-glutamyl]-γ-benzyl-L-glutamate In substantially the same manner as Reference Example 1, the above-titled compound (1.87 g) was obtained from the compound of Reference Example 2 (1.75 g) and the compound of Reference Example 3 (1,385 g).

Specific rotation: $[\alpha]D^{21}$-32.0° (c=1.0, MeOH) $^1$H-NMR (CDCl$_3$)δ: 1.44 (9H,s), 1.72–2.56(16H,m), 3.71(9H,s), 3.73(3H,s), 4.22–4.40(1H,m), 4.53–4.72(3H,m), 5.11(2H,s), 5.36(1H,d,J=9.0 Hz), 6.51(1H,d,J=7.6 Hz), 6.97(1H,d,J=7.6 Hz), 7.34(1H,m), 7.35(5H,s) IR(KBr): 3300, 1740, 1680, 1645, 1535 cm$^{-1}$

Reference Example 6

Production of methyl [N-(tert-butoxycarbonyl)-O$^1$-methyl-γ-L-glutamyl]-L-glutamate To a methanol solution (25 ml) of the compound of Reference Example 4 (830 mg) was added 10% palladium-carbon (85 mg). The mixture was stirred for two hours under hydrogen atmosphere, then the catalyst was filtered off by using celite. The filtrate was subjected to distillation to leave the above-titled compound (710 mg).

Thin-layer chromatography (Silica Gel 60 F$_{254}$, manufactured by E. Merck A. G., in U.S.A., developing solvent; chloroform:methanol=10:1): Rf=0.10

This product was not purified any more, but used in Reference Example 8.

Reference Example 7

Production of methyl [N-(tert-butoxycarbonyl)-O$^1$-methyl-γ-L-glutamyl]-O$^1$-methyl-γ-L-glutamyl]-[O$^1$-methyl-γ-L-glutamyl]-L-glutamate In substantially the same manner as Reference Example 6, the above-titled compound (891 mg) was obtained from the compound of Reference Example 5 (1.018 g).

This-layer chromatography (Silica Gel 60 F$_{254}$, manufactured by E. Merck A. G., in U.S.A., developing solvent; chloroform:methanol=10:1): Rf=0.08

This product was not purified any more, but used in Reference Example 9.

Reference Example 8

Methyl [N-(tert-butoxycarbonyl)-O$^1$-methyl-γ-L-glutamyl]-[O$^1$-methyl-γ-L-glutamyl]-[O$^1$-methyl-γ-L-glutamyl]-[O$^1$-methyl-γ-L-glutamyl]-γ-benzyl-L-glutamate The compound of Reference Example 6 (429 mg) and the compound of Reference Example 3 (514 mg) were dissolved in dry dimethylformamide (7 ml). The solution was cooled to 0° C., and there was added a dry dimethylformamide solution (7 ml) of diethyl cyanophosphate (141 mg). The mixture was stirred for 15 minutes at 0° C., and there was then added dropwise a dry dimethylformamide solution (7 ml) of triethylamine (337 mg). The mixture was stirred for one hour at 0° C., then for 20 hours at room temperature. The reaction mixture was diluted with benzene/ethyl acetate (1/2; 600 ml), washed with 5% hydrochloric acid, water, a saturated aqueous saline solution, a saturated aqueous solution of sodium hydrogencarbonate, water and a saturated aqueous saline solution, successively, then dried over anhydrous magnesium sulfate. The solvent was distilled off under reduced pressure. The residue was recrystallized from chloroform/petroleum ether to give the above-titled compound (584 mg).

Specific rotation: $[\alpha]D^{21}$ −36.6 (c=1.0, MeOH) $^1$H-NMR (CDCl$_3$)δ: 1.46(9H,s), 1.60–2.60(20H,m), 3.67(3H,s), 3.69(6H,s), 3.70(3H,s), 3.75(3H,s), 4.28– 4.76(5H,m), 5.11(2H,s), 5.20–5.30(1H,m), 6.20–6.30(1H,m), 7.05–7.15(1H,m), 7.34(5H,s), 7.30–7.40(1H,m), 7.56–7.63(1H,m) IR(KBr): 3300, 1740, 1680, 1645, 1540 cm$^{-1}$

Reference Example 9

Production of methyl [N-(tert-butoxycarbonyl)-O$^1$-methyl-γ-L-glutamyl]-[O$^1$-γ-L-glutamyl]-[O$^1$-methyl-γ-L-glutamyl]-[O$^1$-γ-L-glutamyl]-[O$^1$ -methyl-γ-L-glutamyl]-γ-benzyl-L-glutamate In substantially the same manner as Reference Example 8, the above-titled compound (878 mg) was obtained from the compound of Reference Example 3 (776 mg).

Specific rotation: $[\alpha]D^{21}$ −39.7 (c=1.0, MeOH) $^1$H-NMR (CDCl$_3$)δ: 1.46(9H,s), 1.77–2.70(24H,m), 3.64(3H,s), 3.67(3H,s), 3.68(3H,s), 3.70(3H,s), 3.72(3H,s), 3.76(3H,s), 4.37–4.80(6H,s), 5.11(2H,s), 5.22(1H,d,J=9.4 Hz), 6.22(1H, d,J=9.4 Hz), 7.17(1H,d,J=9.6 Hz), 7.35(5H,s), 7.43(1H,d,J= 8.6 Hz), 7.55(1H,d,J=8.4 Hz), 7.69(1H,d,J=7.6 Hz) IR(KBr): 3300, 1740, 1650, 1540 cm$^{-1}$

Reference Example 10

Production of [O$^1$-methyl-γ-L-glutamyl]-[O$^1$-γ-L-glutamyl] -γ-benzyl-L-glutamic acid methyl trifluoroacetate To a dichloromethane (10 ml) solution of the compound of Reference Example 4 (230 mg) was added trifluoroacetic acid (0.6 ml). The mixture was stirred for 3 hours at room temperature. Then, the solvent was distilled off under reduced pressure to give the above-titled compound (298 mg).

This product was not purified any more, but used for the production of compounds in Working Examples.

Reference Example 11

Production of [O$^1$-methyl-γ-L-glutamyl]-[O$^1$-γ-L-glutamyl] -[O$^1$-methyl-γ-L-glutamyl]-γ-benzyl-L-glutamic acid methyl trifluoroacetate In substantially the same procedure as Reference Example 10, the above-titled compound (302 mg) was obtained from the compound of Reference Example 5.

This product was not purified any more, but used for the production of compounds in Working Examples.

Reference Example 12

Production of [O$^1$-γ-L-glutamyl]-[O$^1$-methyl-γ-L-glutamyl]-[O$^1$-methyl-γ-L-glutamyl]-[O$^1$-γ-L-glutamyl]-γ-benzyl-L-glutamic acid methyl trifluoroacetate In substantially the same procedure as Reference Example 10, the above-titled compound (140 mg, 100%) was obtained from the compound of Reference Example 8.

This product was not purified any more, but used for the production of compounds in Working Examples.

Reference Example 13

Production of [O$^1$-methyl-γ-L-glutamyl]-[O$^1$-γ-L-glutamyl]-[O$^1$-methyl-γ-L-glutamyl]-[O$^1$-γ-L-glutamyl]-[O$^1$-methyl-γ-L-glutamyl]-γ-benzyl-L-glutamic acid methyl trifluroacetate In substantially the same procedure as Reference Example 10, the above titled compound (562 mg, 100%) was obtained from the compound of Reference Example 9.

This product was not purified any more, but used for the production of compound in Working Examples.

Working Example 1

Production of methyl [N-[4-[3-(2,4-diamino-7H-pyrrolo [2,3-d]pyrimidin-5-yl)propyl]benzoyl]-O$^1$-methyl-γ-L-glutamyl]-γ-benzyl-L-glutamate

[4-[3-(2,4-diamino-7H-pyrrolo[2,3-d]pyrimidin-5 -yl )propyl]benzoic acid (225 mg) and the compound of Reference Example 3 (343 mg) were dissolved in dry dimethylformamide (5 ml). The solution was cooled to 0° C., and there was added a dry dimethylformamide solution (5 ml) o f diethyl cyanophosphate (130 mg). The mixture was stirred for 15 minutes at 0° C., and there was then added dropwise a dry dimethylformamide solution (5 ml) of triethylamine (161 mg). The mixture was stirred for one hour at 0° C., then for 20 hours at room temperature. The solvent was distilled off under reduced pressure, and the residue was purified by means of a silica gel column chromatography [carrier;20 g, developing solvent: chloroform:10% ammonia-containing ethanol=9:1] to give the above-titled compound (292 g)

IR(KBr): 3350, 1730, 1600 cm$^{-1}$ $^1$H-NMR (CDCl$_3$)δ: 1.90–2.39(14H,m), 3.67(3H,s), 3.76(3H,s), 4.59(2H,m), 4.52–4.80(2H,m), 4.94(2H,m), 5.11(2H,s), 6.47(1H,m), 6.98(1H,d,J=8.0 Hz), 7.20–7.36(7H,m), 7.53(1H,d,J=8.0 Hz), 7.75(2H,d,J=8.2 Hz), 8.29(1H,m)

Working Example 2

Production of methyl [N-[4-[3-(2,4-diamino-7H-pyrrolo [2,3-d]pyrimidin-5-yl)propyl]benzoyl]-O$^1$-methyl-γ-L-glutamyl]-[O$^1$-methyl-γ-L-glutamyl]-γ-benzyl-L-glutamate By substantially the same procedure as Working Example 1, the above-titled compound (159 mg) was obtained from 4-[3-(2,4-diamino-7H-pyrrolo[2,3 -d]pyrimidin-5-yl)propyl benzoic acid (120 mg) and the compound of Reference Example 10 (297 mg).

IR(KBr): 3360, 1740, 1650, 1600 cm$^{-1}$ $^1$H-NMR (CDCl$_3$)δ: 1.50–1.71(4H,m), 1.82–2.00(4H,m), 2.02–2.25(2H,m), 2.30–2.43(6H,m), 2.50–2.63(2H,m), 3.61(6H,s), 3.69(3H,s), 4.50(2H,m), 4.43–4.76(3H,m), 5.02(2H,s), 5.17(2H,m), 6.41(1H,s), 7.11–7.40(10H,m), 7.70(2H,d,J=8.0 Hz), 8.58(1H,m)

Working Example 3

Production of methyl [N-[4-[3-(2,4-diamino-7H-pyrrolo [2,3-d]pyrimidin-5-yl)propyl]benzoyl]-O$^1$-methyl-γ-L-glutamyl]-[O-methyl-γ-L-glutamyl]-[O$^1$-methylγ-L-glutamyl]-γ-benzyl-L-glutamate By substantially the same procedure as Working Example 1, the above-titled compound (207 mg) was obtained from 4-[3-(2,4-diamino-7H-pyrrolo[2,3 -d]pyrimidin-5-yl)propyl]benzoic acid (84 mg) and the compound of Reference Example 11 (244 mg).

IR(KBr): 3370, 1740, 1650, 1600 cm$^{-1}$ $^1$H-NMR (CDCl$_3$)δ: 1.60–3.00(22H,m), 3.63(3H,m), 3.70(6H,m), 3.74(3H,s), 4.42(2H,m),4.52–4.87(4H,m), 5.12(2H,s), 5.76(2H,s), 6.52(1H,s),7.20–7.37(9H,m), 7.55(1H,d,J=8.0 Hz), 7.80(2H,d,J=8.2 Hz), 7.85(1H,d,J=8.0 Hz), 9.35(1H,m)

Working Example 4

Production of methyl [N-[4-[3-(2,4-diamino-7H-pyrrolo[2,3-d]pyrimidin-5-yl)propyl]benzoyl]-$O^1$-methyl-γ-L-glutamyl]-[$O^1$-methyl-γ-L-glutamyl]-[$O^1$-methyl-γ-L-glutamyl]-[$O^1$-methyl-γ-L-glutamyl]-γ-benzyl-L-glutamate By substantially the same procedure as Working Example 1, the above-titled compound (360 mg) was obtained from 4-[3-(2,4-diamino-7H-pyrrolo[2,3 -d]pyrimidin-5-yl)propyl]benzoic acid (162 mg) and the compound of Reference Example 12 (575 mg).

IR(KBr): 3400, 1740, 1650, 1610 cm$^{-1}$ $^1$H-NMR (CDCl$_3$)δ: 1.58–2.97(26H,m), 3.64(3H,s), 3.67(3H,s), 3.69(3H,s), 3.71(3H,s), 3.78(3H,s), 4.24(2H,m), 4.51–4.90(5H,m), 5.10(2H,m), 5.90–6.14(2H,m), 6.55(1H, m), 7.17(1H,d,J=8.0 Hz), 7.22–7.42(8H,m), 7.61(1H,m,J= 8.0 Hz), 7.64(1H,d,J=8.0 Hz), 7.76(1H,d,J=8.0 Hz), 7.82(2H,d,J=8.0 Hz), 9.53(1H,m)

Working Example 5

Production of methyl [N-[4-[3-(2,4-diamino-7H-pyrrolo[2,3-d]pyrimidin-5-yl)propyl]benzoyl]-$O^1$-methyl-γ-L-glutamyl]-glutamyl]-[$O^1$-methyl-γ-L-glutamyl]-[$O^1$-γ-L-glutamyl]-γ-benzyl-L-glutamate By substantially the same procedure as Working Example 1, the above-titled compound (271 mg) was obtained from 4-[3-(2,4-diamino-7H-pyrrolo[2,3 -d]pyrimidin-5-yl)propyl]benzoic acid (121 mg) and the compound o f Reference Example 13 (503 mg).

IR(KBr): 3 370, 1740, 1660, 1600 cm$^{-1}$ $^1$H-NMR (CDCl$_3$)δ: 1.60–2.10(6H,m), 2.24–2.90(24H,m), 3.62(3H,s), 3.67(3H,m), 3.68(3H,s), 3.69(3H,s), 3.73(3H,m), 3.79(3H,m), 4.25(2H,m), 4.55–4.76(6H,m), 5.11(2H,s), 5.85(2H,m), 6.54(1H,m), 7.13(1H,d,J=8.0 Hz), 7.20–7.38(8H,m), 7.50–7.70(4H,m), 7.81(2H,d,J=8.2 Hz), 9.32(1H,m)

Working Example 6

Production of [N-[4-[3-(2,4-diamino-7H-pyrrolo[2,3-d]pyrimidin-5-yl)propyl]benzoyl]-γ-L-glutamyl]-L-glutamic acid The compound of Working Example 1 (281 mg) was dissolved in a mixture of water (12 ml) and tetrahydrofuran (8 ml). To the solution was added 1N sodium hydroxide (1.84 ml), and the mixture was stirred for 4 hours at room temperature. Tetrahydrofuran was distilled off under reduced pressure. A small amount of impurities was filtered off with a millipore filter, then the filtrate was neutralized with 1N hydrochloric acid (1.84 ml), which was left standing for a few minutes. Water was removed with a pipette. To the residue was added ether/methanol, then the wall of the vessel was rubbed with a spatula to cause formation of white powder. The powder was collected by filtration and dried to obtain the above-titled compound (157 mg).

IR(KBr): 3340, 3200, 2930, 1730, 1640 cm$^{-1}$ $^1$H-NMR (DMSO-d$_6$)δ: 1.64–2.12(6H,m), 2.26–2.32(4H,m), 2.58–2.71(4H,m), 4.06–4.17(1H,m), 4.22–4.40(1H,m), 5.56(2H,m), 6.16(2H,m), 6.45(1H,s), 7.30(2H,d,J=8.2 Hz), 7.80(2H,d,J=8.2 Hz), 8.12(1H,d,J=8.0 Hz), 8.58(1H,d,J=8.0 Hz), 10.52(1H,m)

Working Example 7

Production of [N-[4-[3-(2,4-diamino-7H-pyrrolo[2,3-d]pyrimidin-5-yl)propyl]benzoyl]-γ-L-glutamyl]-γ-L-glutamyl-L-glutamic acid By substantially the same procedure as Working Example 6, the above-titled compound (187 mg) was obtained from the compound of Working Example 2 (296 mg).

IR(KBr): 3340, 3200, 2930, 1720, 1640 cm$^{-1}$ $^1$H-NMR (DMSO-d$_6$)δ: 1.68–2.00(6H,m), 2.07–2.32(8H,m), 2.62–2.77(4H,m), 4.10 –4.21(2H,m), 4.23–4.42(1H,m), 5.60–5.73(2H,m), 6.31 (2H,m), 6.47(1H,s), 7.30(2H,d,J=8.2 Hz), 7.81(2H,d,J=8.2 Hz), 8.05(1H,d,J=8.0 Hz), 8.13(1H,d,J=8.0 Hz), 8.59(1H,d,J=8.0 Hz), 10.57(1H,m)

Working Example 8

Production of [N-[4-[3-(2,4-diamino-7H-pyrrolo[2,3-d]pyrimidin-5-yl)propyl]benzoyl]-γ-L-glutamyl]-γ-L-glutamyl-γ-L-glutamic acid By substantially the same procedure as Working Example 6, the above-titled compound (137 mg) was obtained form the compound of Working Example 3 (199 mg).

IR(KBr): 3340, 1730, 1650 cm$^{-1}$ $^1$H-NMR (DMSO-d$_6$)δ: 1.65–1.73(18H,m), 2.60–2.78(4H,m), 4.13–4.20(3H,m), 4.25–4.45(1H,m), 5.90–6.10(2H,m), 6.54(1H,m), 6.74(2H, m), 7.30(2H,d,J=8.4 Hz), 7.82(2H,d,J=8.4 Hz), 8.05(1H,d, J=8.0 Hz), 8.10(1H,d,J=8.0 Hz), 8.17(1H,d,J=8.0 Hz), 8.60(1H,d,J=8.0 Hz), 10.78(1H,m)

Working Example 9

Production of [N-[4-[3-(2,4-diamino-7H-pyrrolo[2,3-d]pyrimidin-5-yl)propyl]benzoyl]-γ-L-glutamyl]-γ-L-glutamyl-γ-L-glutamyl-γ-L-glutamyl-L-glutamic acid By substantially the same procedure as Working Example 6, the above-titled compound (127 mg) was obtained from the compound of Working Example 4 (206 mg).

IR(KBr): 3340, 1730, 1650 cm$^{-1}$ $^1$H-NMR (DMSO-d$_6$)δ: 1.55–2.34(22H,m), 2.60–2.80(4H,m), 4.10–4. 21(4H,m), 4.25–4.43(1H,m), 5.90–6.10(2H,m), 6.54(1H,s), 6.78(2H, m), 7.30(2H,d,J=8.4 Hz), 7.84(2H,d,J=8.4 Hz), 8.03–8.26(4H,m), 8.61(1H,d,J=8.0 Hz), 10.82(1H,m)

Working Example 10

Production of [N-[4-[3-(2,4-diamino-7H-pyrrolo[2,3-d]pyrimidin-5-yl)propyl]benzoyl]-γ-L-glutamyl]-γ-L-glutamyl-γ-L-glutamyl-γ-L-glutamyl-γ-L-glutamyl-L-glutamic acid By substantially the same procedure as Working Example 6, the above-titled compound (60 mg) was obtained from the compound of Working Example 5 (126 mg).

IR(KBr): 3340, 1730, 1650 cm$^{-1}$ $^1$H-NMR (DMSO-d$_6$)δ: 1.60–2.40(26H,m), 2.61–2.75(4H,m), 4.07–4.23(5H,m), 4.30–4.40(1H,m), 5.90–6.15(2H,m), 6.54(1H,s), 6.78(2H, m), 7.30(2H,d,J=8.2 Hz), 7.82(2H,d,J=8.2 Hz), 8.00–8.16(5H,m), 8.60(1H,d,J=8.0 Hz), 10.82(1H,m)

Working Example 11

Production of [N-[4-[2-(2,4-diamino-6,7-dihydro-5H-pyrrolo[2,3-d]pyrimidin- 5-yl)ethylthio]benzoyl]-γ-L-glutamyl]-L-glutamic acid By substantially the same procedure as Working Example 1, methyl [N-[4-[2-(2,4-diamino-6,7-dihydro-5H-pyrrolo[2,3-d]pyrimidin- 5-yl)ethylthio]benzoyl]-$O^1$-methyl-γ-L- glutamyl]-γ-benzyl-L-glutamate was synthesized from 4-[2-(2,4-diamino-6,7-dihydro-5H-pyrrolo[2,3-d]pyrimidin-5-yl)ethylthio]benzoic acid (331 mg) and the compound of Reference Example 3 (517 mg). The whole amount of this product was subjected to the same hydrolysis as in Working Example 6 to afford the above-titled compound (294 mg) as a mixture of diastereoisomer.

$^1$H-NMR (Me$_2$SO-d$_6$)δ: 1.62–1.80(2H,m), 1.82–2.20(6H, m), 2.21–2.37(2H,m), 2.90–3.03(2H,m), 3.22–3.37(2H,m), 3.45–3.62(1H,m), 4.03–4.18(1H,m), 4.23–4.37(1H,m), 6.23(1H, bs), 6.31(1H, bs), 6.46(1H, bs), 6.55(1H, bs), 6.90(1H,s), 7.31(1H,d,J=9 Hz), 7.33(1H,d,J=9 Hz), 7.77(1H,d,J=9 Hz), 7.79(1H, d,J=9 Hz), 8.10(0.5H,d,J=8 Hz), 8.17(0.5H,d, J=8 Hz), 8.63(0.5H,d,J=8 Hz), 8.69(0.5H, d,J=8 Hz), 10.6 0(1H,s)

Working Example 12

Production of [N-[4-[3-(2-amino-4-hydroxy-7H-pyrrolo[2,3-d]pyrimidin- 5-yl)propyl]benzoyl]-γ-L-glutamyl]-L-glutamic acid By substantially the same procedure as Working Example 1, methyl N-[4-[3-(2-amino-4-hydroxy-7H-pyrrolo[2,3-d]pyrimidin- 5-yl)propyl]benzoyl]-O$^1$-methyl-γ-L-benzyl-L-glutamate was synthesized from 4-[3-(2-amino-4-hydroxy-7H-pyrrolo[2,3-d]pyrimidin-5-yl)propyl]benzoic acid (313 mg) and the compound of Reference Example 3 (517 mg). The whole amount of this product was subjected to the same hydrolysis as in Working Example 6 to afford the above-titled compound (282 mg).

$^1$H-NMR (DMSO-d$_6$)δ: 1.78–2.17(6H,m), 2.23–2.41(4H, m), 2.53–2.80(4H,m), 4.01–4.12(1H,m), 4.30–4.47(1H,m), 5.92(2H,s), 6.36(1H,s), 7.28(2H,d,J=8 Hz), 7.79(2H,d,J=8 Hz), 8.12(1H,d,J=7.8 Hz), 8.55(1H,d,J=7.8 Hz), 10.10(1H, s)

Working Example 13

Production of N-[4-[N-[2-(2,4-diamino-6,7-dihydro-5H-pyrrolo[2,3-d]pyrimidin- 5-yl)ethyl]-N-methylamino]benzoyl]-γ-L-glutamyl]-L-glutamic acid By substantially the same procedure as Working Example 1, methyl N-[4-[N-[2-(2,4-diamino-6,7-dihydro-5H-pyrrolo[2,3-d]pyrimidin-5-yl)ethyl]-N-methylamino]benzoyl-O$^1$-methyl-γ-L-glutamyl]-γ-benzyl-L-glutamate was synthesized from 4-[N-[2-(2,4-diamino-6,7-dihydro-5H-pyrrolo[2,3-d]pyrimidin-5-yl)ethyl]-N-methylamino]benzoic acid (329 mg) and the compound of Reference Example 3 (517 mg). The whole amount of this product was subjected to the same hydrolysis as in Working Example 6 to afford the above-titled compound (276 mg).

$^1$H-NMR (DMSO-d$_6$+D$_2$O)δ: 1.41–1.65(1H,m), 1.75–2.11 (5H,m), 2.28(4H, t,J=7 Hz), 2.93(3H,s), 3.13–3.45 (4H,m), 3.52–3.66(1H,m), 3.99–4.12(1H,m), 4.20–4.34 (1H,m), 6.72(2H, dd,J=9 Hz, 2 Hz), 7.71(2H,d, J=9 Hz)

Working Example 14

Production of [N-[5-[3-(2,4-diamino-7H-pyrrolo[2,3-d]pyrimidin- 5-yl)propyl]-2-thenoyl]-γ-L-glutamyl]-L-glutamic acid By substantially the same procedure as Working Example 1, methyl [N-[5-[3-(2,4-diamino-7H-pyrrolo[2,3-d]pyrimidin- 5-yl)propyl]-2-thenoyl]-O$^1$-methyl-γ-L-glutamyl]-γ-benzyl-L-glutamate was synthesized from 5-3-(2,4-diamino-7H-pyrrolo[2,3-d]pyrimidin-5-yl)propyl]-2-thiophene carboxylic acid trifluoroacetic acid salt (431 mg) and the compound of Reference Example 3 (517 mg). The whole amount of this product was subjected to the same hydrolysis as in Working Example 6 to afford the above-titled compound (305 mg).

$^1$H-NMR (DMSO-d$_6$)δ: 1.76–2.18(6H,m), 2.27–2.40(4H, m), 2.70(2H, t,J=7.6 Hz), 2.85(2H, t,J=7.6 Hz), 4.02–4.14 (1H,m), 4.24–4.37(1H,m), 5.60(2H,s), 6.21(2H,s), 6.47(1H, s), 6.87(1H,d,J=3.6 Hz), 7.68(1H,d,J=3.6 Hz), 8.10(1H,d,J= 7.6 Hz), 8.51(1H,d,J=7.6 Hz), 10.52(1H,s)

Working Example 15

[N-[4-[2-(2-amino-4-hydroxy-7H-pyrrolo[2,3-d]pyrimidin- 5-yl)ethyl] benzoyl]-γ-L-glutamyl]-L-glutamic acid By substantially the same procedure as Working Example 1 and 6, the above-titled compound was obtained.

$^1$H-NMR (Me$_2$SO-d$_6$)δ: 1.76–2.15(4H,m), 2.20–2.33(4H, m), 2.78–3.03(4H,m), 4.12–4.22(1H,m), 4.28–4.41(1H,m), 6.01(2H,s), 6.32(1H,d,J=2.0 Hz), 7.28(2H,d,J=8.0 Hz), 7.78(2H,d,J=8.0 Hz), 8.06(1H,d,J=8.0 Hz), 8.52(1H,d,J=8.0 Hz), 10.16(1H,s), 10.60(1H,s)

Working Example 16

[N-[4-[N-2-(2-amino-4-hydroxy-7H-pyrrolo[2,3-d]pyrimidin- 5-yl)ethylamino]benzoyl]-γ-L-glutamyl]-L-glutamic acid By substantially the same procedure as Working Example 1 and 6, the above-titled compound was obtained.

$^1$H-NMR (Me$_2$SO-d$_6$+D$_2$O)δ: 1.79–2.14 (4H,m), 2.21–2.35 (4H,m), 2.85(2H, t,J=7.0 Hz), 3.31(2H, t,J=7.0 Hz), 4.10–4.22(1H,m), 4.31–4.43(1H,m), 6.50(1H,s), 6.63(2H,d,J=8.8 Hz), 7.65(2H,d,J=8.8 Hz)

Working Example 17

[N-[4-[N-[2-(2-amino-4-hydroxy-7H-pyrrolo[2,3-d]pyrimidin- 5-yl)ethyl]-N-methylamino]benzoyl]-γ-L-glutamyl]-L-glutamic acid By substantially the same procedure as Working Example 1 and 6, the above-titled compound was obtained.

$^1$H-NMR (Me$_2$SO-d$_6$+D$_2$O)δ: 1.77–2.15(4H,m), 2.20–2.35 (4H,m), 2.77(2H, t,J=7.4 Hz), 2.98(3H,s), 3.66(2H, t,J=7.4 Hz), 4.09–4.20(1H,m), 4.31–4.45(1H,m), 6.43(1H,d,J=1.8 Hz), 6.88(2H,d,J=8.8 Hz), 7.76(2H,d,J=8.8 Hz)

Working Example 18

[N-[4-[N-[2-(2-amino-4-hydroxy-7H-pyrrolo[2,3-d]pyrimidin- 5-yl)ethyl]-N-propargylamino]benzoyl]-γ-L-glutamyl]-L-glutamic acid By substantially the same procedure as Working Example 1 and 6, the above-titled compound was obtained.

$^1$H-NMR (Me$_2$SO-d$_6$+D$_2$O)δ: 1.78–2.15(4H,m), 2.20–2.36 (4H,m), 2.86(2H,m), 3.12(1H,s), 3.66(2H,m), 4.10–4.21 (1H,m), 4.19(2H,s), 4.32–4.46(1H,m), 6.47(1H, d,J=2.0 Hz), 6.99(2H,d,J=9.0 Hz), 7.77(2H,d,J=9.0 Hz)

Working Example 19

[N-[5-[N-[2-(2-amino-4-hydroxy-7H-pyrrolo[2,3-d]pyrimidin- 5-yl)ethyl]-N-methylamino]-2-thenoyl]-γ-L-glutamyl]-L-glutamic acid By substantially the same procedure as Working Example 1 and 6, the above-titled compound was obtained.

$^1$H-NMR (Me$_2$SO-d$_6$+D$_2$O)δ: 1.80–2.16(4H,m), 2.18–2.33 (4H,m), 2.79(2H,m), 3.05(3H,s), 3.64(2H,m), 4.07–4.19 (1H,m), 4.33–4.22(1H,m), 5.94(1H,d,J=4.4 Hz), 6.49(1H,d,J=2.0 Hz), 7.56(1H,d,J=4.4 Hz)

Working Example 20

[N-[5-[N-[2-(2-amino-4-hydroxy-7H-pyrrolo[2,3-d]pyrimidin- 5-yl)ethyl-N-propargylamino]-2-thenoyl]-γ-L-glutamyl]-L-glutamic acid By substantially the same procedure as Working Example 1 and 6, the above-titled compound was obtained.

$^1$H-NMR (Me$_2$SO-d$_6$+D$_2$O)δ: 1.79–2.14 (4H,m), 2.19–2.34 (4H,m), 2.85(2H,m), 3.10(1H,s), 3.65(2H,m), 4.11–4.23 (1H,m), 4.18(2H,s), 4.34–4.45(1H,m), 6.05(1H, d,J=4.4 Hz), 6.50(1H,d,J=2.0 Hz), 7.58(2H,d,J=4.4 Hz)

Working Example 21

[N-[4-[N-[2-(2-amino-4-hydroxy-7H-pyrrolo[2,3-d]pyrimidin- 5-yl)ethyl]-N-methylamino]-2-fluorobenzoyl]-γ-L-glutamyl]-L-glutamic acid By substantially the same procedure as Working Example 1 and 6, the above-titled compound was obtained.

$^1$H-NMR (Me$_2$SO-d$_6$+D$_2$O)δ: 1.75–2.17(4H,m), 2.22–2.36 (4H,m), 2.76(2H,m), 2.99(3H,s), 3.64(2H,m), 4.05–4.18 (1H,m), 4.29–4.43(1H,m), 6.40(1H, dd,J=2.2, 14.8 Hz), 6.48(1H,s), 6.50(1H, dd,J=2.2, 8.6 Hz), 7.75(1H, t,8.6 Hz)

Working Example 22

[N-[4-[N-[2-(2-amino-4-hydroxy-7H-pyrrolo[2,3-d]pyrimidin- 5-yl)ethyl]-N-propargylamino]-2-fluorobenzoyl]-γ-L-glutamyl]-L-glutamic acid By substantially the same procedure as Working Example 1 and 6, the above-titled compound was obtained.

$^1$H-NMR (Me$_2$SO-d$_6$+D$_2$O)δ: 2.87(2H,m), 3.09(1H,s), 3.66(2H,m), 4.04–4.19(1H,m), 4.20(2H,s), 4.33– 4.43(1H, m), 6.42(1H, dd,J=2.2, 14.8 Hz), 6.47(1H,s), 6.51(1H, dd,J= 2.2, 8.6 Hz), 7.74(1H, t,J=8.6 Hz)

Working Example 23

N-[4-[N-[2-(2-amino-4-hydroxy-7H-pyrrolo[2,3-d]pyrimidin- 5-yl)ethyl]-N-propargylamino]-2chlorobenzoyl]-γ-L-glutamyl]-L-glutamic acid By substantially the same procedure as Working Example 1 and 6, the above-titled compound was obtained.

$^1$H-NMR (Me$_2$SO-d$_6$+D$_2$O)δ: 1.79–2.20(4H,m), 2.23–2.38 (4H,m), 2.84(2H,m), 3.15(1H,s), 3.65(2H,m), 4.19(2H,s), 4.06–4.20(1H,m), 4.27–4.43(1H,m), 6.46(1H,s), 7.00(1H,d,J=8.8 Hz), 7.01(1H,s), 7.33(1H,d,J=8.8 Hz)

What is claimed is:

1. A compound of the formula

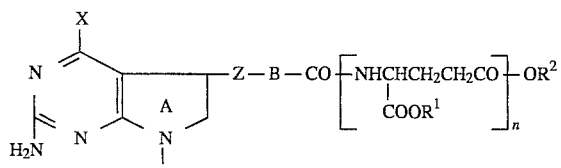

wherein ring Ⓐ stands for a pyrrole or pyrroline;

B stands for

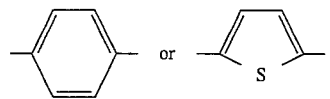

X stands for an amino group, hydroxyl group, or mercapto group;

Z stands for —CH$_2$CH$_2$—, —CH$_2$CH$_2$CH$_2$—, —CH$_2$$_l$ s—, —CH$_2$CH$_2$NH—, —CH$_2$CH$_2$N(CH$_3$)—, or —CH$_2$CH$_2$N(CH$_2$C≡CH)—;

COOR$^1$ and COOR$^2$ independently stand for a carboxyl group which may be esterified with (1) a C$_{1-5}$ alkyl, (2) a benzyl group which may be substituted with a nitro group or C$_{1-4}$ alkoxy group, or (3) a phenyl group which may be substituted with a nitro group or C$_{1-4}$ alkoxy group;

n denotes an integer of 2 to 6 and R$^1$ may be different in each of the n repeating units, or a pharmaceutically acceptable salt thereof.

2. A compound as claimed in claim 1, wherein X is an amino group and Z is trimethylene.

3. An anti-tumor composition which comprises an effective amount of a compound as claimed in claim 1 or a pharmaceutically acceptable salt thereof, together with a pharmaceutically acceptable carrier or carriers.

4. An agent for inhibiting thymidylic acid synthase, 5-aminoimidazole-4-carboxyamide ribonucleotide transformylase or growth of Meth A fibrosarcoma cell which comprises an effective amount of a compound as claimed in claim 1 or a pharmaceutically acceptable salt thereof.

5. A method for treating tumor which comprises administrating an effective amount of a compound as claimed in claim 1 or its pharmaceutically acceptable salt together with a pharmaceutically acceptable carrier or diluent to a mammal.

6. A compound as claimed in claim 1, wherein X stands for amino group.

7. A compound as claimed in claim 1, wherein X stands for hydroxyl group.

8. A compound as claimed in claim 1, wherein Z stands for ethylene.

9. A compound as claimed in claim 1, wherein Z stands for trimethylene.

10. A compound as claimed in claim 1, wherein COOR$^1$ and COOR$^2$ independently stand for a carboxyl group which may be esterified with (1) a C$_{1-5}$ alkyl group, or (2) a benzyl group.

11. A compound as claimed in claim 1, wherein n denotes an integer of 2 or 3.

12. A compound as claimed in claim 1, wherein X stands for hydroxyl group, and Z stands for dimethylene.

13. A compound of claim 1 which is [N-[4-[N-[2-(2-amino-4-hydroxy-7H-pyrrolo[2,3-d] pyrimidin-5-yl)ethyl]-N-propargylamino]benzoyl]-γ-L-glutamyl]-L-glutamic acid.

* * * * *

UNITED STATES PATENT AND TRADEMARK OFFICE
CERTIFICATE OF CORRECTION

PATENT NO. : 5,459,129
DATED : October 17, 1995
INVENTOR(S) : Hiroshi AKITOMO

It is certified that error appears in the above-indentified patent and that said Letters Patent is hereby corrected as shown below:

Please note that Column 29, Line 59, Claim 1,

" 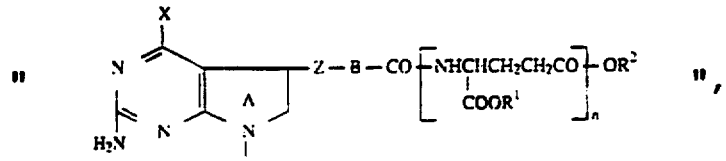 ", should read --

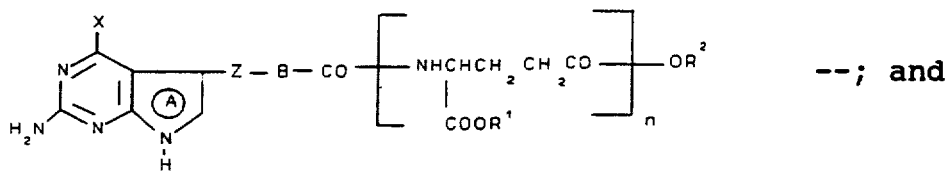 --; and

Column 30, lines 13-14, Claim 1, delete "—$CH_2S$—, —$CH_2CH_2NH$—," and insert ---$CH_2S$--, --$CH_2CH_2NH$--,--.

Signed and Sealed this

Fourteenth Day of May, 1996

Attest:

BRUCE LEHMAN

Attesting Officer

Commissioner of Patents and Trademarks